(12) United States Patent
Carter et al.

(10) Patent No.: US 10,408,725 B2
(45) Date of Patent: Sep. 10, 2019

(54) SUBSTRATE-INTEGRATED HOLLOW WAVEGUIDE SENSORS

(71) Applicants: Lawrence Livermore National Security, LLC, Livermore, CA (US); Universität Ulm, Ulm (DE)

(72) Inventors: Jerry Chance Carter, Livermore, CA (US); Michael P. Chrisp, Lexington, MA (US); Anastacia M. Manuel, Dublin, CA (US); Boris Mizaikoff, Ulm (DE); Andreas Wilk, Blaustein (DE); Seong-Soo Kim, Ulm (DE)

(73) Assignee: Lawrence Livermore National Security, LLC, Livermore, CA (US)

( * ) Notice: Subject to any disclaimer, the term of this patent is extended or adjusted under 35 U.S.C. 154(b) by 353 days.

(21) Appl. No.: 13/631,936

(22) Filed: Sep. 29, 2012

(65) Prior Publication Data
US 2013/0081447 A1    Apr. 4, 2013

Related U.S. Application Data

(60) Provisional application No. 61/542,162, filed on Oct. 1, 2011.

(51) Int. Cl.
| | |
|---|---|
| *G02B 6/032* | (2006.01) |
| *G01N 9/00* | (2006.01) |
| *G01N 9/24* | (2006.01) |
| *G01N 21/47* | (2006.01) |
| *G01N 21/05* | (2006.01) |
| *G01N 21/35* | (2014.01) |
| *G02B 6/10* | (2006.01) |

(Continued)

(52) U.S. Cl.
CPC ............. *G01N 9/00* (2013.01); *G01N 9/24* (2013.01); *G01N 21/05* (2013.01); *G01N 21/35* (2013.01); *G01N 21/474* (2013.01); *G02B 6/10* (2013.01); *G01N 21/3504* (2013.01); *G01N 21/3577* (2013.01); *G01N 2021/0346* (2013.01); *G01N 2021/052* (2013.01); *G01N 2021/058* (2013.01); *G01N 2021/3595* (2013.01); *G02B 6/032* (2013.01)

(58) Field of Classification Search
CPC .......................... G01N 21/3504; G02B 6/032
USPC ........................................................ 385/132
See application file for complete search history.

(56) References Cited

U.S. PATENT DOCUMENTS

| | | |
|---|---|---|
| 5,440,664 A | 8/1995 | Harrington et al. |
| 5,567,471 A | 10/1996 | Harrington et al. |

(Continued)

OTHER PUBLICATIONS

Bernini et al., "Integrated Silicon Optical Sensors Based on Hollow Core Waveguide", Proc. of SPIE, vol. 6477, 2007, pp. 647714-1-647714-14.

(Continued)

*Primary Examiner* — Charlie Y Peng
(74) *Attorney, Agent, or Firm* — John P. Wooldridge

(57) ABSTRACT

Methods and apparatuses are provided that greatly expand the utility of conventional hollow waveguide-based sensors via either straight, substrate-integrated channels or via meandering (e.g., circuitous, curved or folded optical paths) waveguide sensor designs. Full- or hybrid-integration of the meandering hollow waveguide with light source, detector, and light-guiding optics facilitates compact yet high-performance gas/vapor and/or liquid sensors of the substrate-integrated hollow waveguide sensor.

23 Claims, 25 Drawing Sheets

(51) Int. Cl.
*G01N 21/03* (2006.01)
*G01N 21/3504* (2014.01)
*G01N 21/3577* (2014.01)

(56) References Cited

U.S. PATENT DOCUMENTS

| | | | |
|---|---|---|---|
| 5,574,100 A | 11/1996 | Sagane et al. | |
| 5,729,646 A | 3/1998 | Miyagi et al. | |
| 5,995,696 A | 11/1999 | Miyagi et al. | |
| 6,018,390 A * | 1/2000 | Youmans et al. | 356/477 |
| 7,304,732 B1 * | 12/2007 | Polcawich | G01N 21/1702 |
| | | | 250/339.07 |
| 7,574,089 B1 * | 8/2009 | Zribi et al. | 385/129 |
| 8,472,761 B2 * | 6/2013 | Rosenberg | G02B 6/43 |
| | | | 362/551 |
| 2005/0089262 A1 * | 4/2005 | Jenkins | G02B 6/122 |
| | | | 385/14 |
| 2006/0182384 A1 * | 8/2006 | Jenkins et al. | 385/14 |
| 2008/0231857 A1 * | 9/2008 | Depeursinge et al. | 356/437 |
| 2011/0013866 A1 * | 1/2011 | Rosenberg | G02B 6/0096 |
| | | | 385/14 |

OTHER PUBLICATIONS

Bernini et al., Silicon Micromachined Hollow Optical Waveguides for Sensing Applications, IEEE Journal on Selected Topics in Quantum Electronics, vol. 8, No. 1, 2002, pp. 106-110.
Davis et al., "The Future of Sensors and Instrumentation for Human Breath Analysis", IEEE Sensors Journal, vol. 10, No. 1, 2010, pp. 3-6.
Frey et al., "Near-Infrared Hollow Waveguide Gas Sensors", Applied Spectroscopy, vol. 65, No. 11, 2011, pp. 1269-1274.
Harrington, "A Review of IR Transmitting, Hollow Waveguides", Fiber and Integrated Optics, 19, 2000, pp. 211-217.
Harrington, "Infrared Hollow Waveguides: An Update", Proc. of SPIE, vol. 6852, 2008, pp. 68520M-1-68520M-8.
Jenkins et al., "Hollow Optical Waveguide Devices and Systems", Proc. of SPIE, vol. 7113, 2008, pp. 71130E-1-71130E-8.
Kim et al., "Miniaturized Mid-infrared Sensor Technologies", Anal. Bioanal. Chem., 2008, pp. 390:231-237.
Kim et al., "Mid-Infrared Trace Gas Analysis with Single-Pass Fourier Transform Infrared Hollow Waveguide Gas Sensors", Applied Spectroscopy, vol. 63, No. 3, 2009, pp. 331-337.
Kim et al., "Potential and Challenges for Mid-Infrared Sensors in Breath Diagnostics", IEEE Sensors Journal, vol. 10, No. 1, 2010, pp. 145-158.
Kriesel et al., "Hollow Core Fiber Optics for Mid-Wave and Long-Wave Infrared Spectroscopy", SPIE Defense, Sensing, and Security in (CBRNE) Sensing XII, Paper #8018-31, 2011, 10 pp.
Kumar et al., "Tunable Hollow Optical Waveguide and its Applications", Frontiers in Guided Wave Optics and Optoelectronics, www.itechopen.com, 2010, pp. 343-363.
Saito et al., "Infrared Optical Fiber Sensors", Optical Review, vol. 4, No. 5, 1997, pp. 527-538.
Thompson et al., "Characterization of a Mid-Infrared Hollow Waveguide Gas Cell for the Analysis of Carbon Monoxide and Nitric Oxide", Applied Spectroscopy, vol. 60, No. 3, 2006, pp. 266-271.
Webster et al., Determining the Local Abundance of Martian Methane and its' 13C/12C and D/H Isotopic Ratios for Comparison with Related Gas and Soil Analysis on the 2011 Mars Science Laboratory (MSL) Mission, Planetary and Space Science, 59, 2011, pp. 271-283.
Wilk et al., "Toward the Quantification of the 13CO2/12CO2 Ratio in Exhaled Mouse Breath with Mid-infrared Hollow Waveguide Gas Sensors", Anal. Bioanal. Chem., 2012, pp. 402:397-404.
Young et al., "External Cavity Widely Tunable Quantum Cascade Laser Based Hollow Waveguide Gas Sensors for Multianalyte Detection", Sensors and Actuators, B, 140, 2009, pp. 24-28.
Young et al., Infrared Hollow Waveguide Sensors for Simultaneous Gas Phase Detection of Benzene, Toluene, and Xylenes in Field Environments, Anal. Chem., 83, 2011, pp. 6161-6147.

* cited by examiner

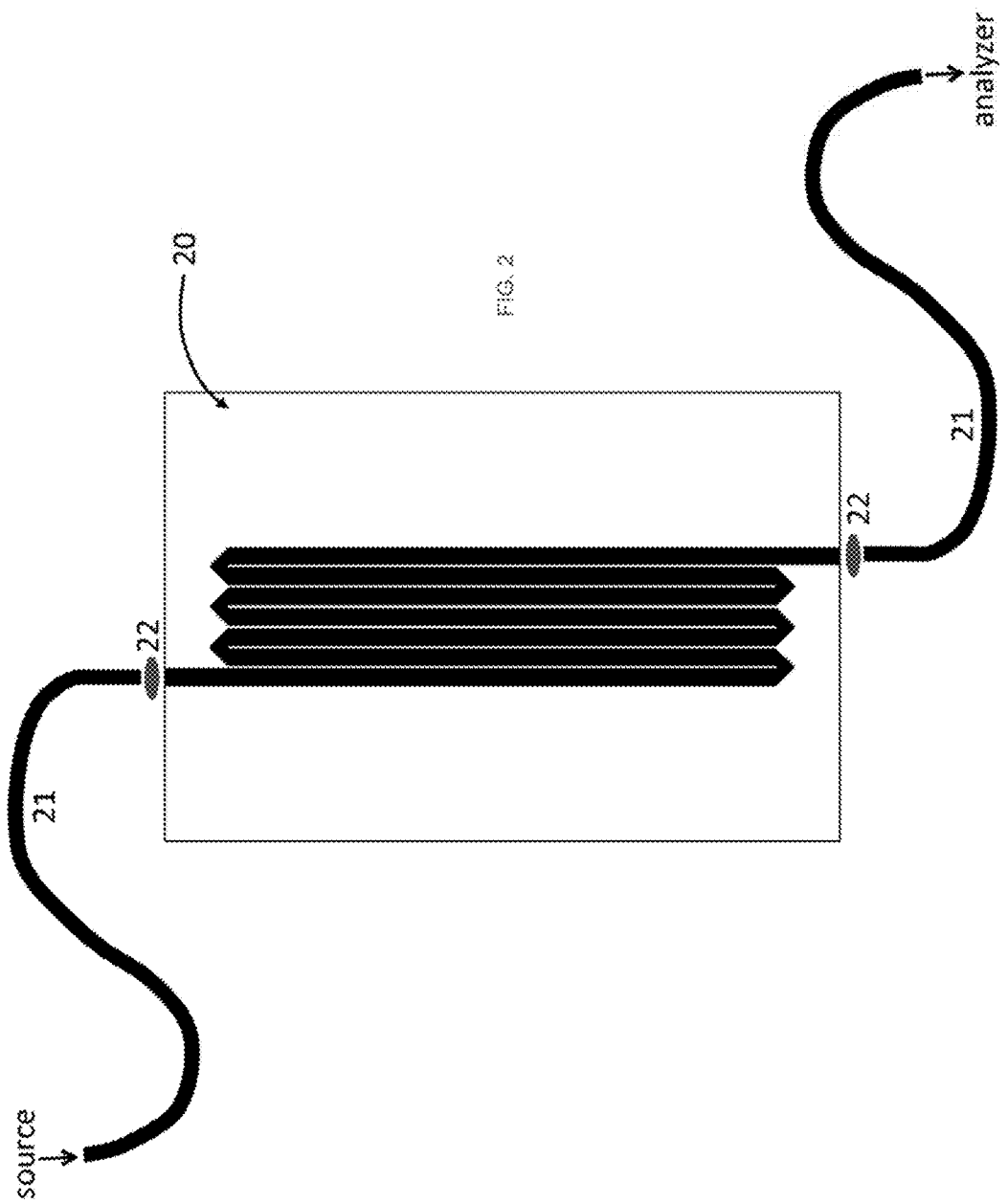

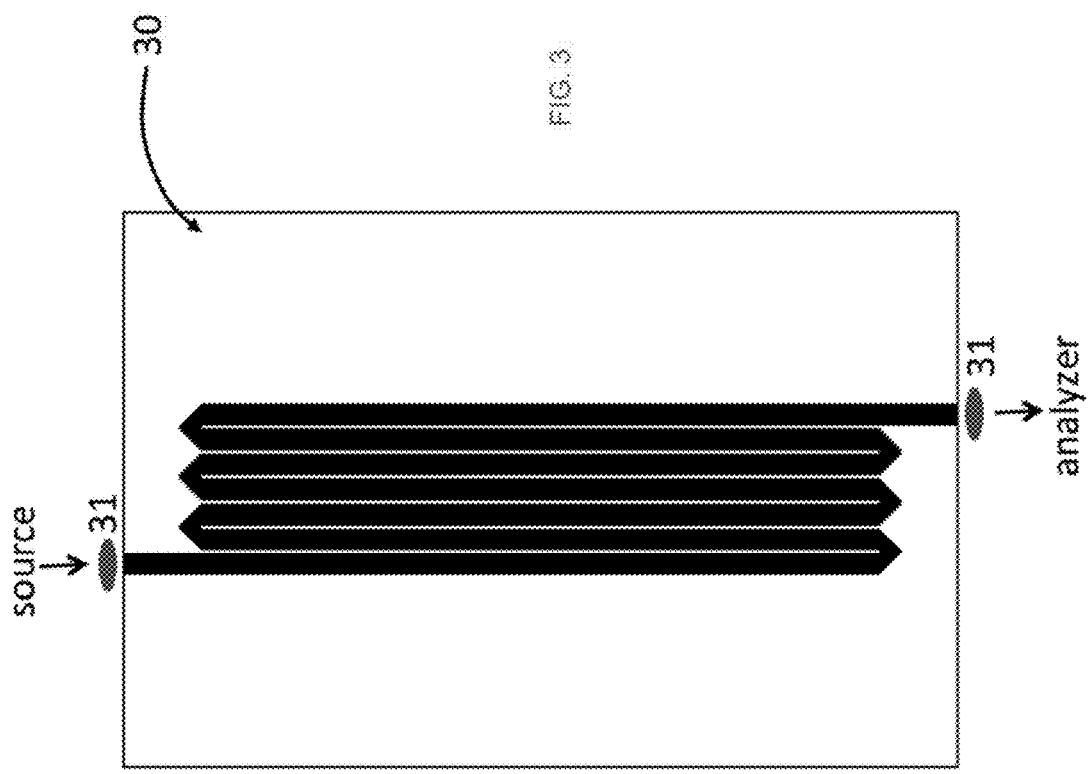

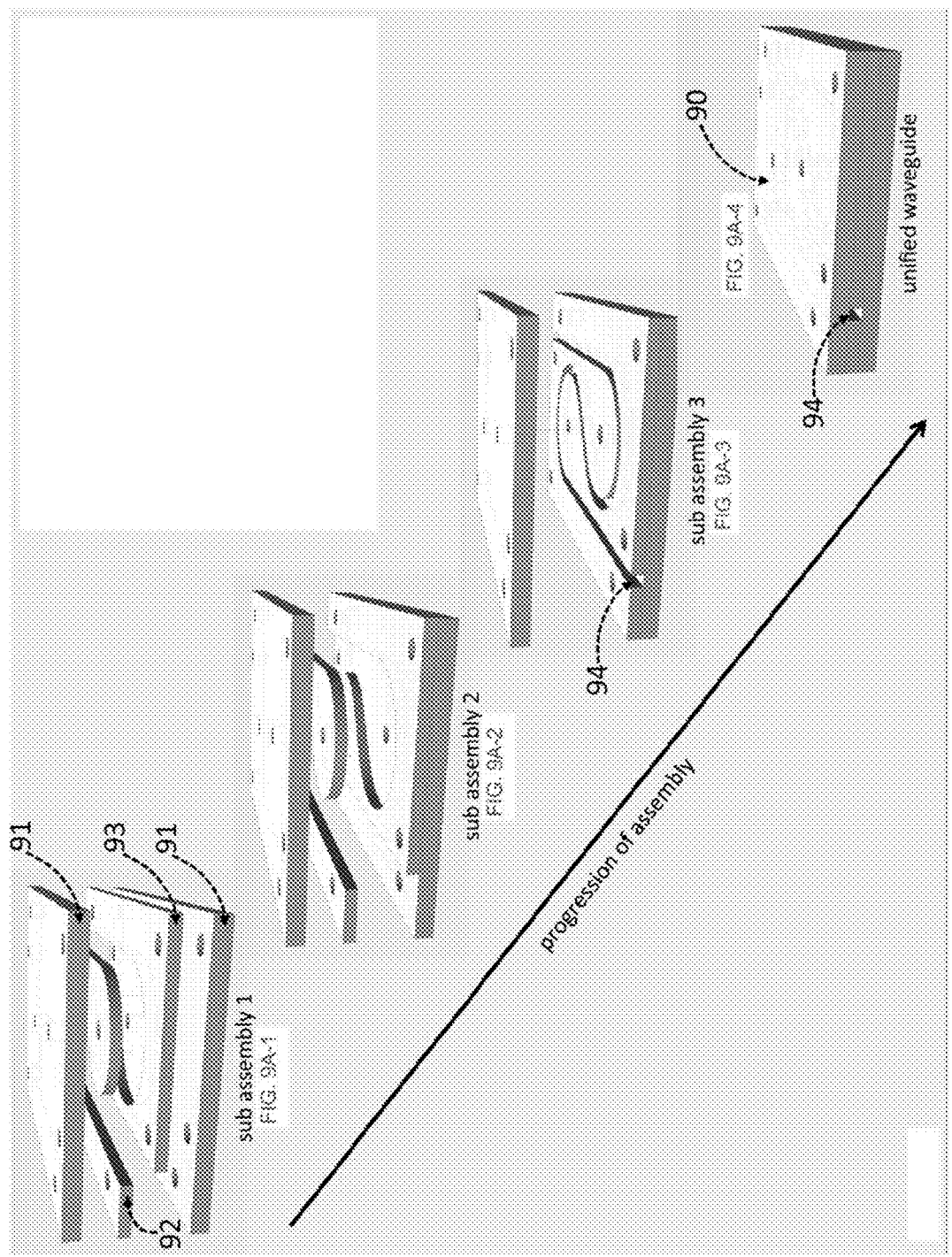

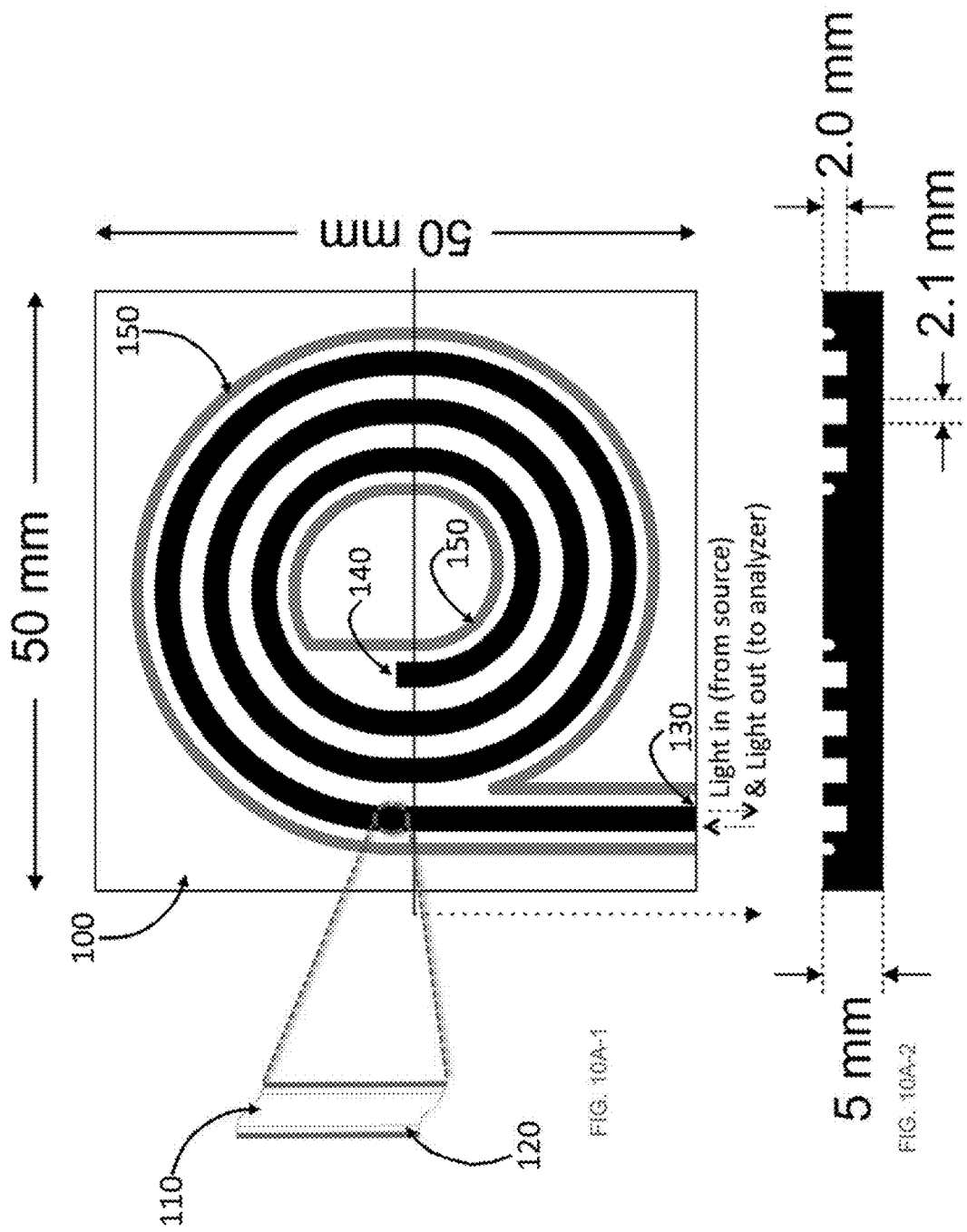

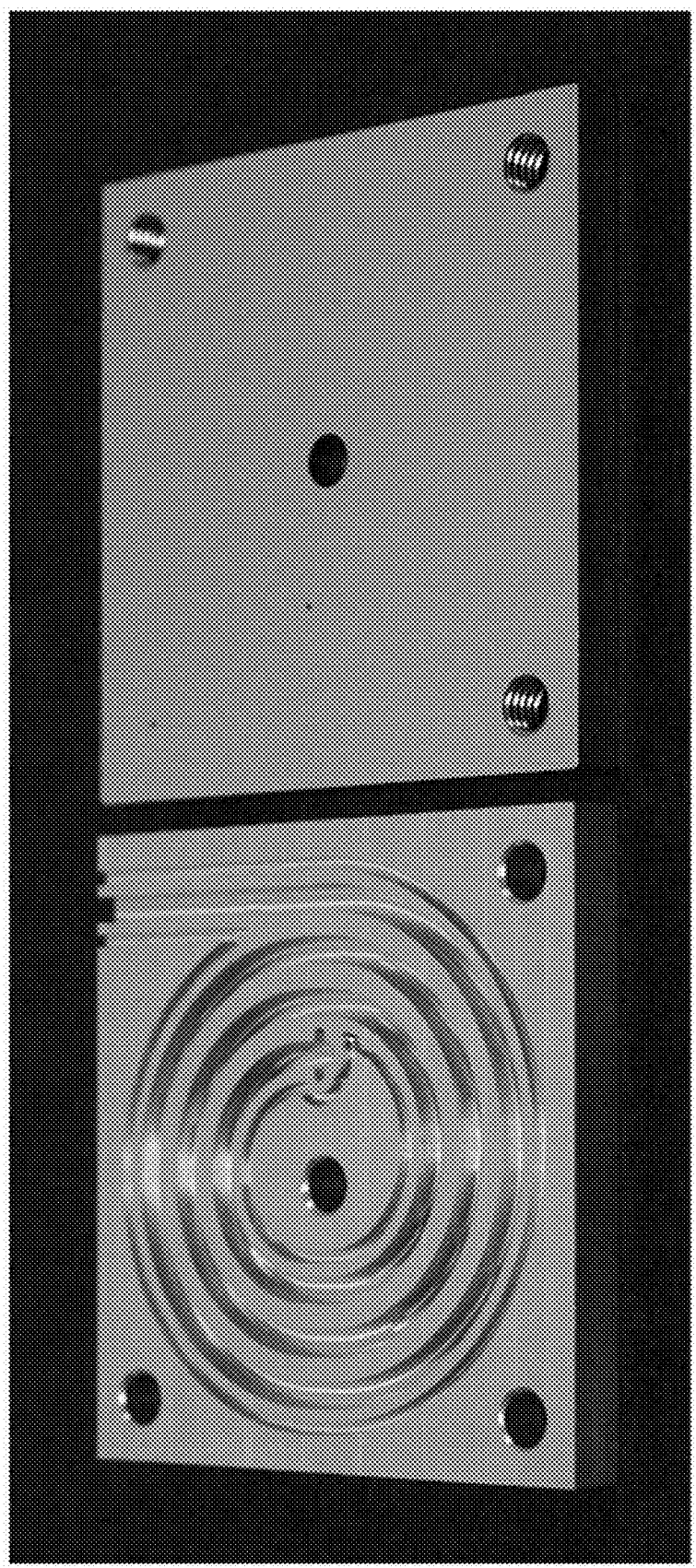

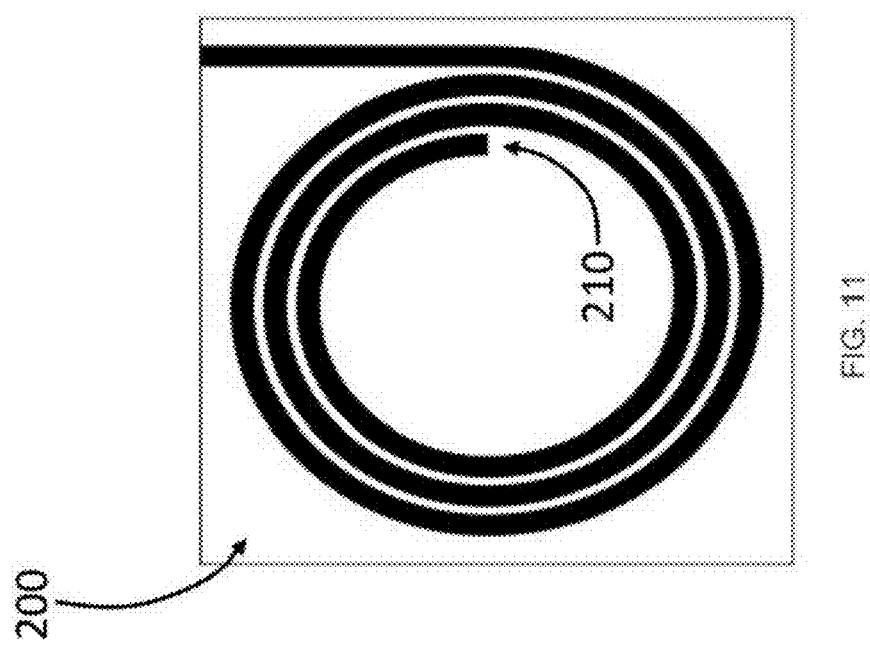

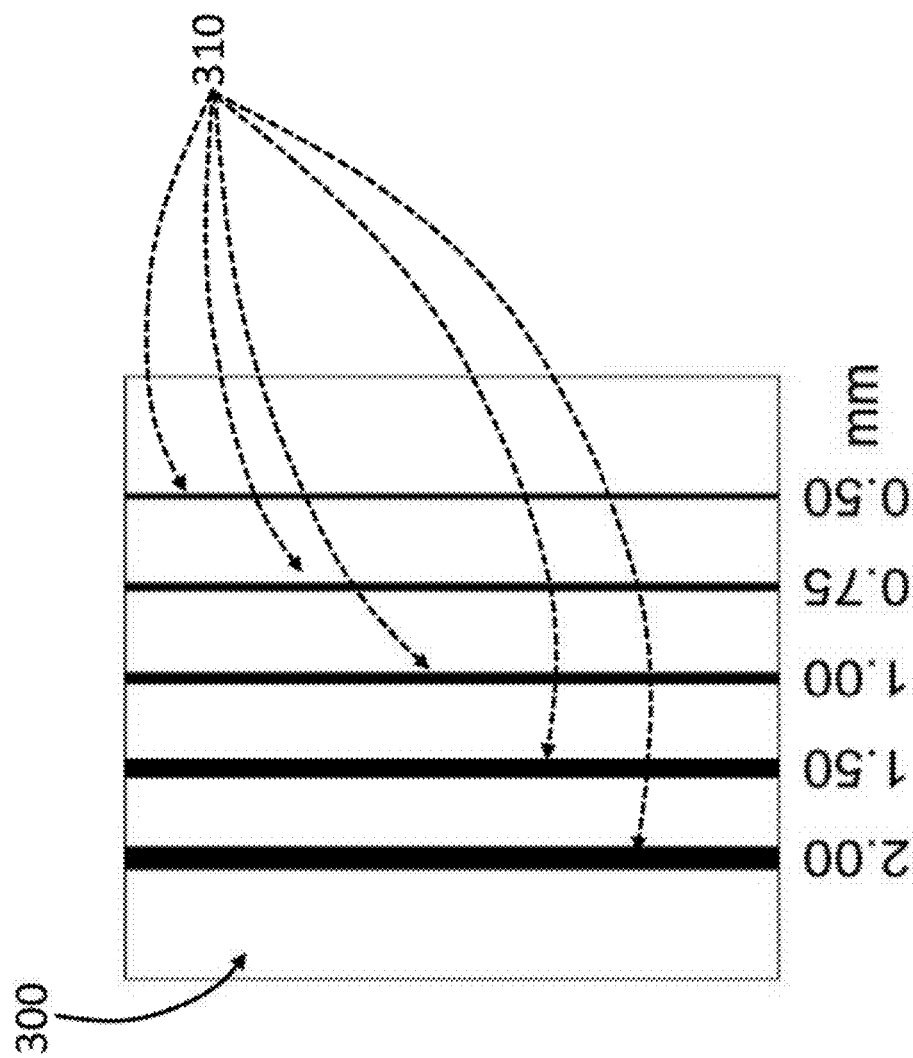

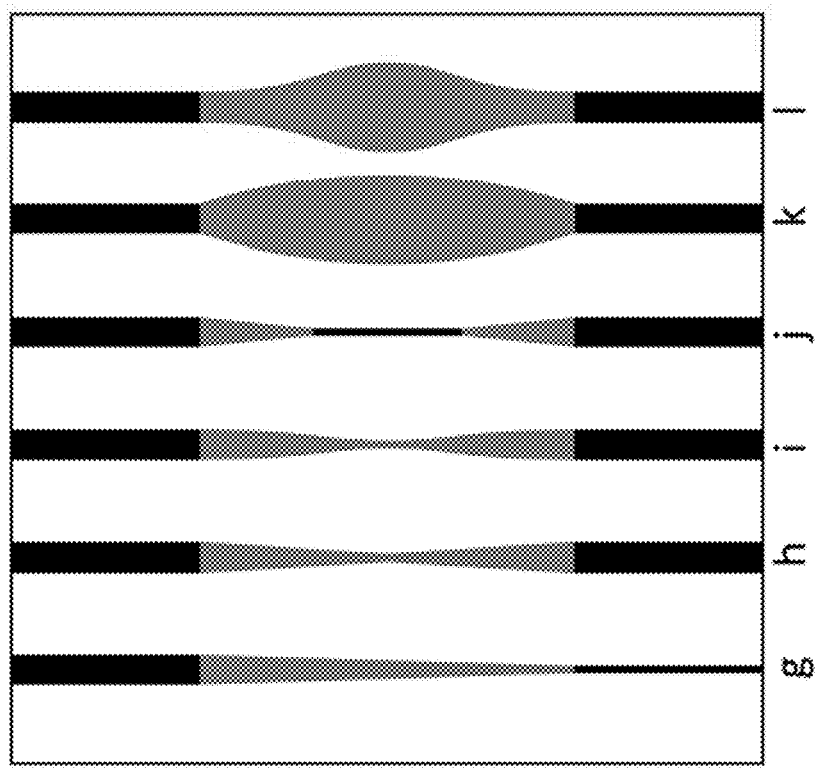
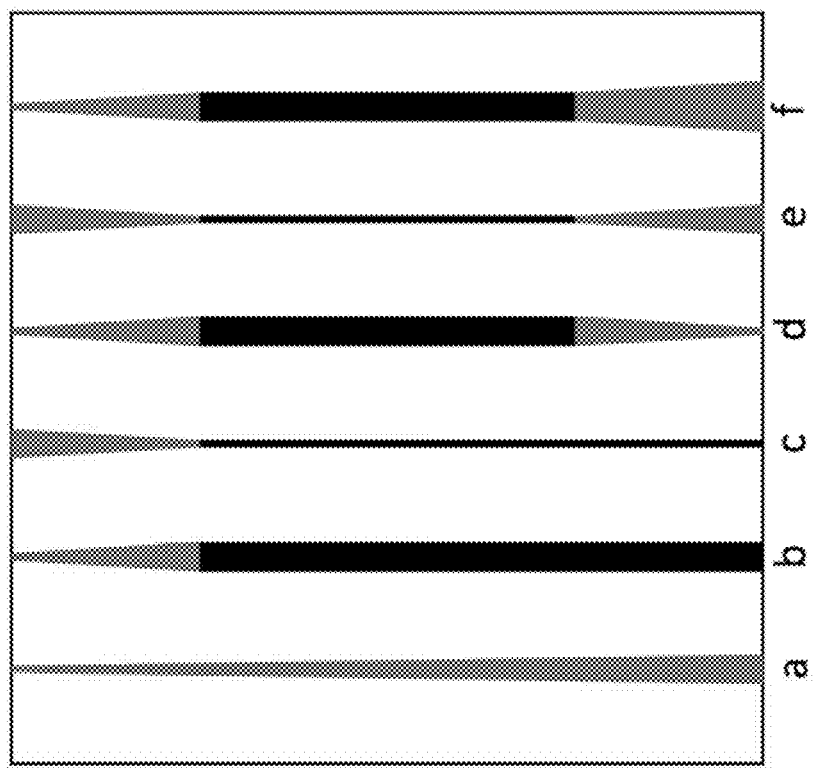
FIG. 15

SUBSTRATE-INTEGRATED HOLLOW WAVEGUIDE SENSORS

CROSS-REFERENCE TO RELATED APPLICATIONS

This application claims the benefit of U.S. Provisional Patent Application No. 61/542,162 titled "Substrate-Integrated Hollow Waveguide Sensors," filed 1 Oct. 2011, incorporated herein by reference.

STATEMENT REGARDING FEDERALLY SPONSORED RESEARCH OR DEVELOPMENT

The United States Government has rights in this invention pursuant to Contract No. DE-AC52-07NA27344 between the U.S. Department of Energy and Lawrence Livermore National Security, LLC, for the operation of Lawrence Livermore National Laboratory.

BACKGROUND OF THE INVENTION

Field of the Invention

The present invention relates to hollow waveguide sensors, and more specifically, it relates to substrate-Integrated hollow waveguide sensors.

Description of Related Art

Conventional hollow waveguides as they are known by those knowledgeable in the field were first developed as a conduit for transmitting laser light for industrial and biomedical applications. Those applications relied on hollow waveguide length (i.e., often meters), flexibility, and a high damage threshold. In recent years as their use has extended to include spectroscopic applications, the adopted conventional hollow waveguides are not suitable for integration into sensing devices because of two key characteristics, length and flexibility. For example in high-sensitivity infrared (IR) gas sensing applications involving hollow waveguide sensors, the prior art requires a large operational footprint because the conventional hollow waveguides must be physically long (typically 0.5 to 4 meters in length of drawn tubular glass having an optical coating at the inside of the hollow core), because physical length is needed to increase the sampling path length to obtain trace levels of detection for gas analytes. The flexible conventional hollow waveguide must also be supported over these lengths and in a manner that ideally maintains a constant temperature and eliminates vibrations, either of which can alter the light guiding modes of the waveguide.

In the prior art, the dimensions of the waveguide largely govern the size of the overall gas sensor, thereby limiting its practical use for many applications. In the prior art, coiling the waveguide has been demonstrated to reduce its form factor, however, the results show substantial signal attenuation due to bending losses (attenuation coefficient varies as 1/R, where R is the bending radius). Furthermore, there are no long-term studies to show how the internal stresses in a coiled conventional hollow waveguide affect the overall lifetime of the waveguide.

The prior art devices rely on drawn glass tubes, capillary tubes, rolled tubes, parallel metal plates, plastic tubes, or other extruded shapes to co-locate electromagnetic radiation and a gas/vapor or liquid over a pre-determined path length thereby causing the analyte of interest to interact with the light to detect and quantify the analyte(s) present. Prior art devices with high performance (e.g., sensitivity) tend to be large in size and expensive. Hollow waveguides of circular geometry made of metal, glass, or plastic tubing and having diameters of 1 millimeter or less and lengths ranging from 1-4 meters (for high sensitive applications) are common today; those made of silica are commercially available and have been demonstrated to have the lowest losses compared to other prior art examples. Prior art devices can be made to be small but at the expense of sensitivity (e.g., bending losses) and robustness (e.g., internal bending stresses on materials and optical coatings). Prior art devices are dependent on wet-chemistry for internal coatings, which limits the variety of the internal coating options. Prior art devices are therefore not appropriate solutions in applications where small size, high sensitivity, low cost, integration with other sensor components or peripheral components, and long-term robustness are required.

SUMMARY OF THE INVENTION

The invention is substrate-integrated hollow waveguide sensors. Some embodiments include meandering hollow waveguides for use in gas/vapor and or liquid sensing applications based-on, but not limited to, infrared and Raman spectroscopies. The meandering hollow waveguide is used as a key component in substrate-integrated hollow waveguide sensors comprising 1) a light source, such as a laser or on-coherent source (e.g. SiC filament, etc.) which could be coupled directly via optics or via an optical fiber or array of fibers or other hollow waveguide for the transmission of light to the sensor, which is then placed in such a manner as to contact the sample to be measured; 2) a return fiber or array of fibers or other hollow waveguide or direct optical coupling for returning the light (e.g. scattered, absorbed, etc.) from the sample to a spectroscopic analyzing instrument such as a spectrometer. The substrate-integrated hollow waveguide sensors comprising the meandering hollow waveguide are both disclosed in this invention and consist of any one of a number of including combinations of the following: 1) optics for filtering light; 2) optics for focusing and/or refocusing light, 3) optics for collecting light, 4) optics for reflecting light; 5) optical fibers or arrays of fibers or hollow waveguides; 6) optics for interfacing optical fibers or arrays or other hollow waveguides; 7) heating devices and controllers; 8) insulating layers; 9) clamping devices; 10) light source, and 11) analyzer. An enclosure, ideally sealed from the environment except where the gas/vapor or liquid analyte may penetrate through, containing the optical component, is also a feature of the invention.

BRIEF DESCRIPTION OF THE DRAWINGS

The accompanying drawings, which are incorporated into and form a part of the disclosure, illustrate embodiments of the invention and, together with the description, serve to explain the principles of the invention.

FIG. 2 is a diagrammatic representation of one of several embodiments of the substrate integrated hollow waveguide sensor configured with a serpentine type meandering hollow waveguide and optical fiber couplings.

FIG. 3 is a diagrammatic representation of one of several embodiments of the substrate-integrated hollow waveguide sensor configured with a serpentine type meandering hollow waveguide and optical couplings.

FIG. 9A-1 through 9A-4 are diagrammatic representations of the assembly of one of a modular meandering hollow waveguide of the substrate-integrated hollow waveguide sensor.

FIG. 9C-1 is an overlay of the gas/vapor, flow cell, sensor with the hollow channels of the spiral type meandering waveguide.

FIG. 9C-2 is design drawing of the waveguide of FIG. 9C-1.

FIG. 10A-1 is a top view diagrammatic representation of one of several multi-pass spiral type meandering hollow waveguide embodiments of the substrate-integrated hollow waveguide sensor.

FIG. 10A-2 is a side view diagrammatic representation of the embodiment of FIG. 10A-1.

FIG. 10B-C are reduction to practice images of the uncoated multi-pass spiral type meandering hollow waveguide embodiment of FIG. 10a and a polished gold-coated plate, respectively, such that when combined these form a meandering waveguide having a channel with four orthogonal surfaces.

FIG. 11 is a diagrammatic representation of one of several alternate spiral type meandering hollow waveguide embodiments of the substrate-integrated hollow waveguide sensor.

FIG. 12 is a diagrammatic representation of a straight type hollow waveguide with channels of varying dimensions.

FIG. 15 shows a variety of hollow waveguide tapered and widened/expanded channels.

DETAILED DESCRIPTION OF THE INVENTION

Glossary

The following terms are intended to have the following general meanings as they are used herein:

Meandering hollow waveguide for meandering waveguide): Refers to either, substrate-integrated channels or via meandering (e.g., circuitous, curved or in any way, shape or form folded optical paths) waveguide sensor designs.

Light: energy which may be selectively applied including energy having a wavelength between $2 \times 10^{-7}$ and $1 \times 10^{-1}$ meters including for example, deep ultraviolet radiation, ultraviolet radiation, visible radiation, near infrared radiation, mid infrared radiation, and far infrared radiation.

Source: Refers to devices that produce coherent and/or incoherent light Examples include, but are not limited to, lasers (e.g., quantum cascade, gas, solid state, fiber), globars, diodes, and SiC filaments.

Analyzer: Refers to a single device or combination of devices that provide wavelength and/or frequency selection and detection. Examples of wavelength and/or frequency selection devices include, but are not limited to, Fourier-transform infrared spectrometers (FTIR), other non-dispersive spectrometers, dispersive spectrometers, tunable filters. Examples of detection devices include, but are not limited to, charge-coupled devices (CCD), intensified-charge coupled devices (ICCD) or other photodiodes, photomultiplier tubes (PMT), mercury cadmium telluride (MCT) or other photoconductive detectors, photovoltaic detectors, deuterated triglycin sulfate (DTGS) detectors or other thermal/pyroelectric detectors.

Backreflection (with regard to a meandering hollow waveguide): Refers to light reflected back toward the source from somewhere within the meander waveguide. This can be desirable in the case of a double-pass meandering hollow waveguide where a retro-reflector or mirror is positioned at a channel port or within the meander waveguide for this intended purpose. For single-pass meandering hollow waveguide designs, this is not desirable and represents an unwanted loss since this fraction of light does not reach the analyzer.

Sensor: Refers to a device that comprises, at a minimum, a waveguide/transducer, source, analyzer, and optical elements for coupling/interfacing the waveguide, source, and analyzer.

Substrate: a material/solid having a rigid or semi-rigid surface.

Port: Refers to a meandering waveguide channel opening where light is either coupled into or out of the device.

Analyte: Refers to the chemical species (e.g., gas/vapor molecules) to be determined in the analytical measurement.

Figure 1:
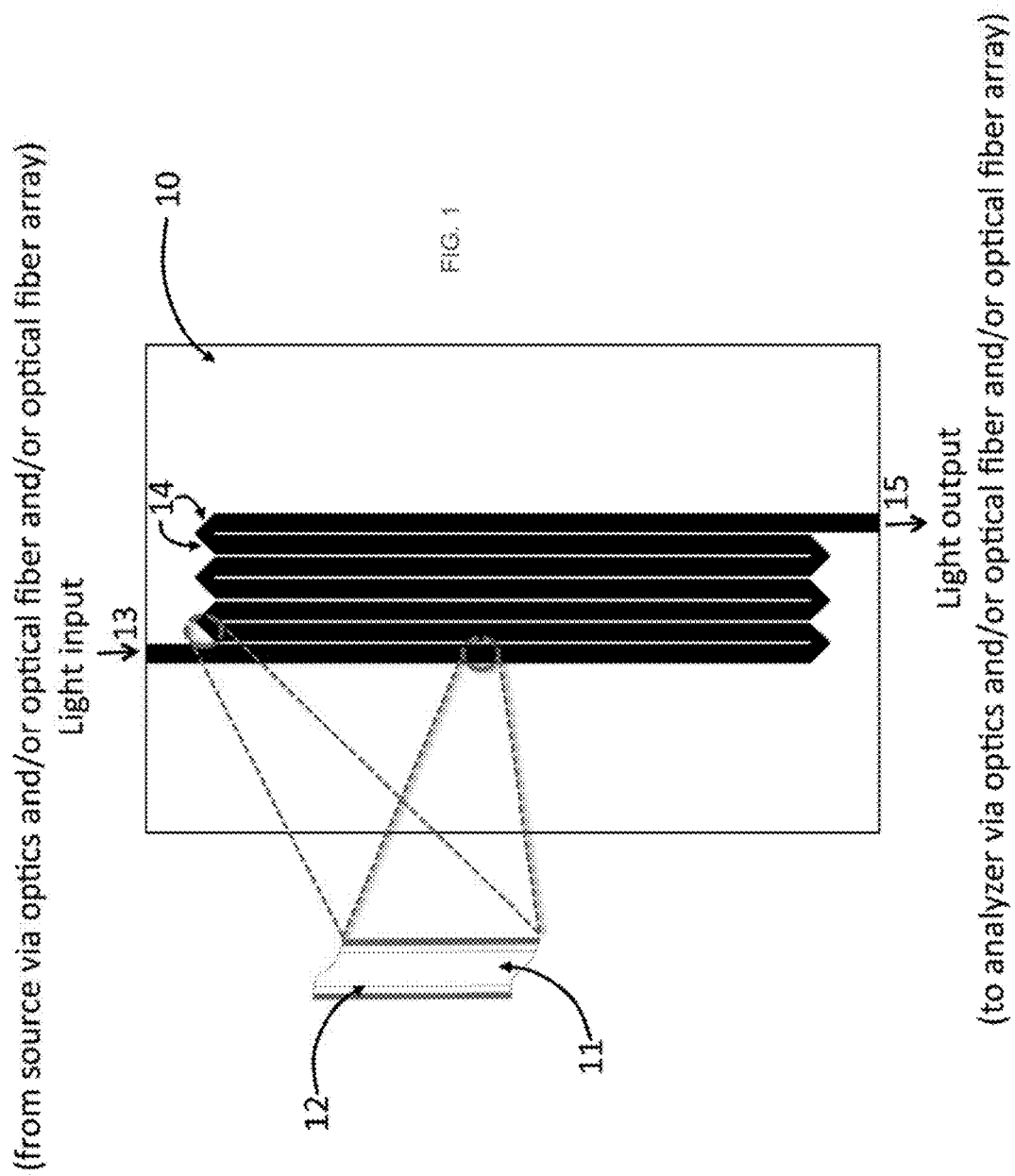
FIG. 1 is a diagrammatic representation of one of several serpentine type in meandering hollow waveguide embodiments of the substrate-integrated hollow waveguide sensor.

FTIR: Fourier-transform infrared.
MCT: mercury cadmium telluride
PEEK: polyether ether ketone
PC: polycarbonate
PMMA: polymethyl methacrylate (i.e., acryl glass)
PTFE: polytetrafluoroethylene
FEP: fluorinated ethylene propylene
MBE: molecular beam epitaxy PECVD: plasma enhanced chemical vapor deposition
CVD: chemical vapor deposition
MOCVD: metal organic chemical vapor deposition Details of One Embodiment as a Meandering Hollow Waveguide for Use with Collimated Light in a Substrate-Integrated Hollow Waveguide Sensor A diagrammatic representation of one configuration of a meandering hollow waveguide 10 is shown in FIG. 1. The figure shows rectangular (2×2.1 mm) hollow channels 11 in a serpentine (i.e., winding) arrangement and having an internal channel surface treatment 12 and/or channel modifications (e.g., chemo- or biolayers, immobilized enzymes, antigen/antibodies) such that the overall device can be coupled to a source and analyzer forming the basis of the substrate-integrated hollow waveguide sensor for conducting gas/vapor and/or liquid optical measurements, performed remotely (e.g., coupling via an optical fiber or fiber array or combinations that include optics) or non-remotely (e.g., coupling via optics) and/or in situ using, but not limited to, infrared absorption or Raman scattering spectroscopy techniques. The hollow channel of the meandering waveguide serves as both a miniature gas/vapor or liquid cell and as a 'light pipe' for directing and constraining the light and importantly for co-locating the light and analyte(s). In the case of mid-infrared (mid-IR) absorption, the interaction path length of gas/vapor molecules with the light is related to the amount of light absorbed. Under suitable conditions, the absorbance is directly proportional to the gas/vapor concentration through Beer's Law ($A=abc$), where 'a' is the molecule specific absorption coefficient, 'b' is the interaction path length, and 'c' is the gas/vapor concentration. By varying the length and/or number of channels, the optical path length can be tailored to meet the sensitivity requirements of a specific sensing application.

In operation, light from a source, such as a laser which is the source for the FIG. 1 design, is directed to one of two meandering waveguide channel openings (e.g., ports) 13 via a fiber or fiber array or conventional optics (see FIGS. 2 and 3) or combinations thereof. The light entering the waveguide channel opening 13 would ideally be perfectly collimated (i.e., no divergence) such that no light would interact with the walls of the waveguide channel but rather propagate through all meandering waveguide channels via interactions (e.g., reflections) at only the angled (e.g., 45 degree is shown) features 14 of each straight channel. In this way, losses due to reflection and/or light scattering and/or non-analyte absorption are minimized; in some cases this arrangement may also result in a reduction of interfering background signal levels. As the light traverses the entire path length of the hollow channels, it interacts with gas/vapor and/or liquid phase molecules co-located in the hollow channels via a plurality of ways to be discussed later (Section XII). Light exiting the waveguide channel port 15 is directed via a fiber or fiber array or conventional optics (see FIGS. 2 and 3) or combinations thereof to the analyzer where the interactions (e.g. absorption, Raman scattering) between the light and molecules are recorded. It is also important to note that either port of the FIG. 1 meandering waveguide embodiment can serve as the light in-coupling or light out-coupling port from/to the source and analyzer, respectively.

Figure 9B:
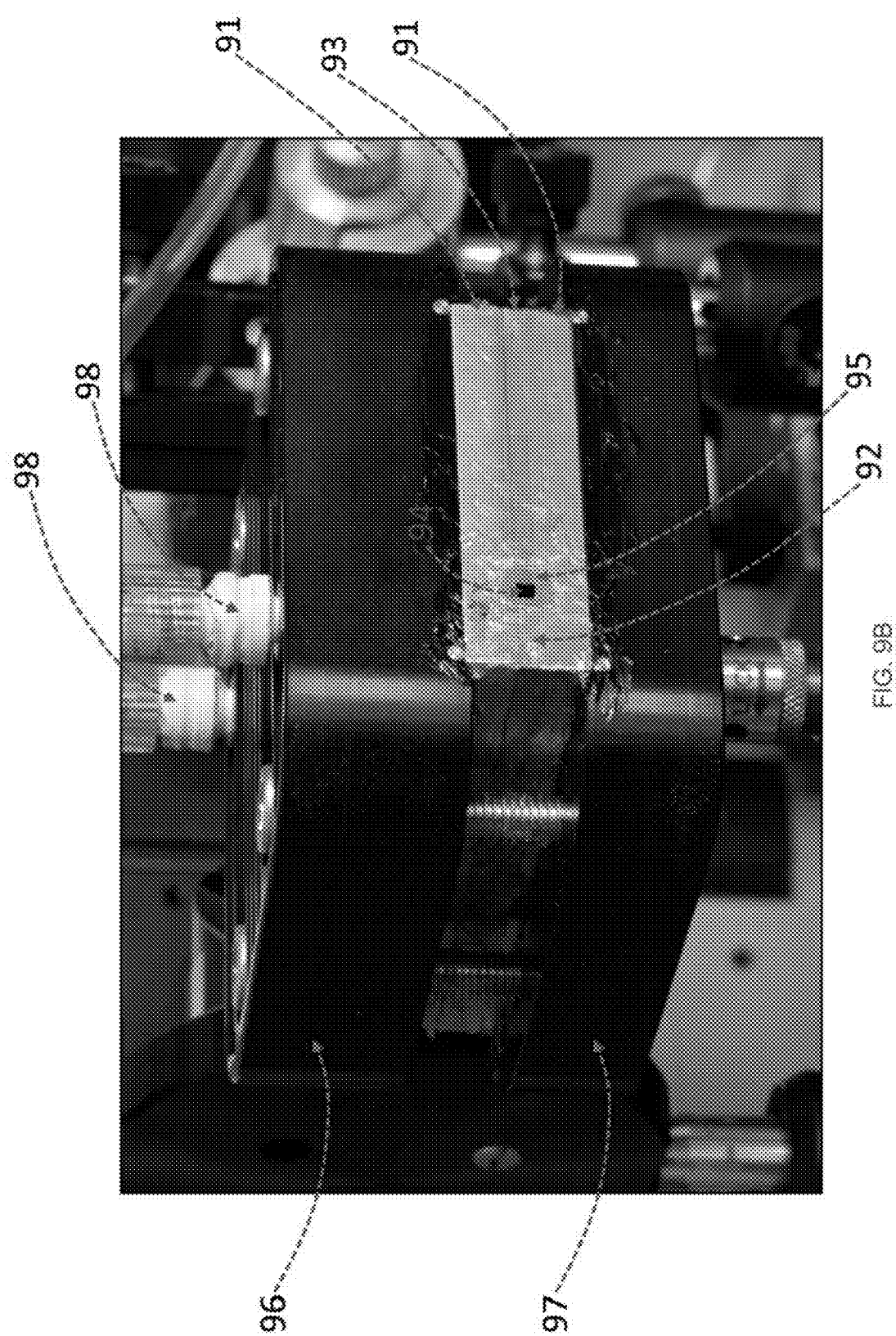
FIG. 9B is an image of a gas/vapor, flow cell, sensor comprising a spiral type modular hollow waveguide.
Figures 1, 2, 9C:
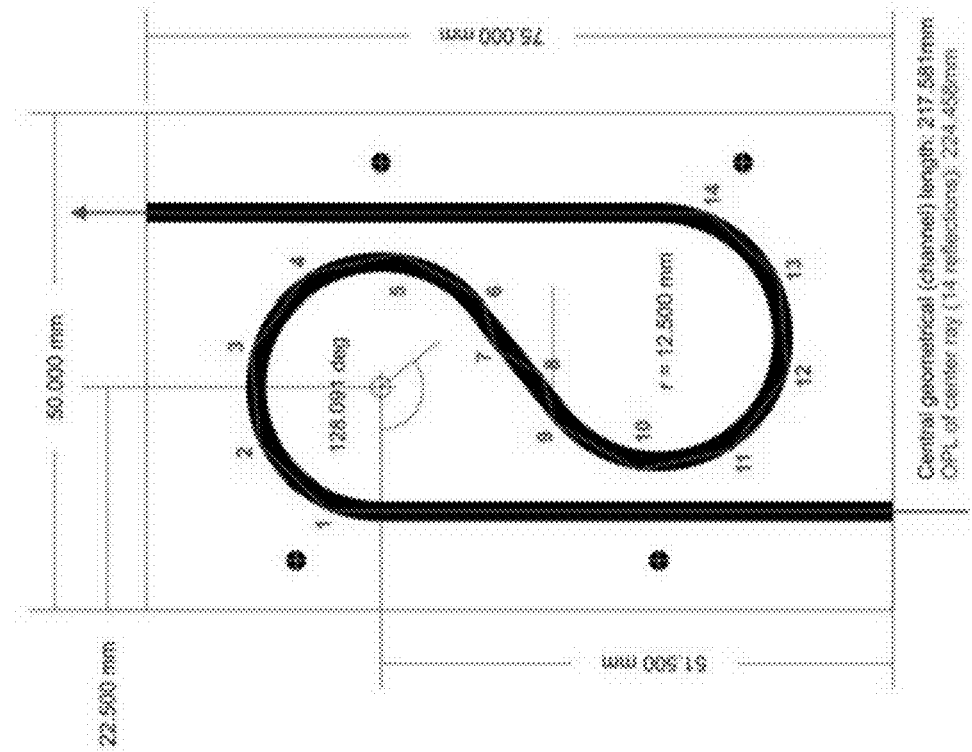

FIG. 2 is a diagrammatic representation of a serpentine meander waveguide 20 (described in FIG. 1) interfaced to the source and analyzer using optical fibers and/or fiber arrays and/or a combination of fibers 21 and optics 22, forming the basis of the substrate-integrated hollow waveguide sensor. The type fibers depicted in FIG. 2 include, but are not limited to silica fibers, sapphire, fluoride glasses, chalcogenide glasses, germanium sulfide glasses, semiconductors, halide fibers, other crystalline fibers (i.e., polycrystalline, single crystal), and other hollow waveguide fibers. The optics 22 depicted in FIG. 2 represent single element or multi-element lens combinations and/or mirrors (e.g., off-axis parabolic) and/or other optical elements such as special filters, etc. FIG. 3 is a diagrammatic representation of the serpentine meander waveguide 30 (described in FIG. 1) but without fibers. Here optics 31 are used to interface the meander waveguide to the source and analyzer forming the basis of the substrate-integrated hollow waveguide sensor.

Upon review of this disclosure, other embodiments will be apparent to those skilled in the art; the description given is not intended to be restrictive. For example, the light in-coupling and light out-coupling ports for the meander waveguide of FIGS. 1, 2, and 3 could be fabricated such that both channel ports are positioned on the same side, adjacent sides, or on opposite sides in a different configuration. The FIG. 4 embodiment is an example of the latter. Furthermore, an optic (e.g., reflector, grating, etc.) could be placed at one channel opening to direct light through the waveguide channels a second time forming a multi-pass (e.g double-pass in the simplest case) configuration.

Figure 5:
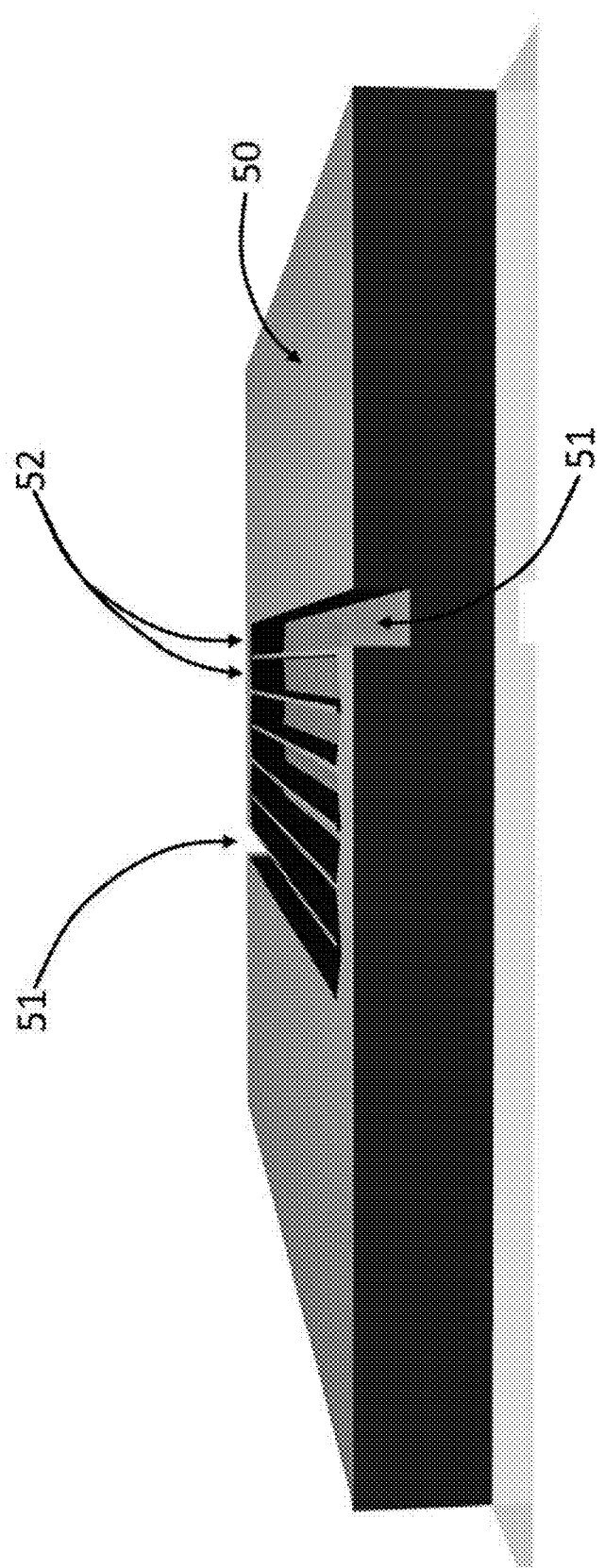
FIG. 5 is a 3-dimensional diagrammatic representation of the serpentine type meandering hollow waveguide of FIG. 1-3.

The use of highly collimated light for the meandering waveguide design of FIGS. 1, 2, and 3 would enable the elimination of at least one channel surface (i.e., the top and/or bottom channel surface) of the meander hollow channel allowing rapid movement of molecules into the light path constrained within the hollow channel geometry. FIG. 5 is a diagrammatic 3-dimensional representation of the serpentine type meander waveguide 50 of FIGS. 1, 2, and 3 without a top channel surface enclosing the hollow channel. FIG. 5 shows the meander channel ports 51 where light is coupled into and out of the hollow channels of the meandering waveguide and the angled (e.g., 45 degree is shown) features 52 of the straight channels.

Figure 6:
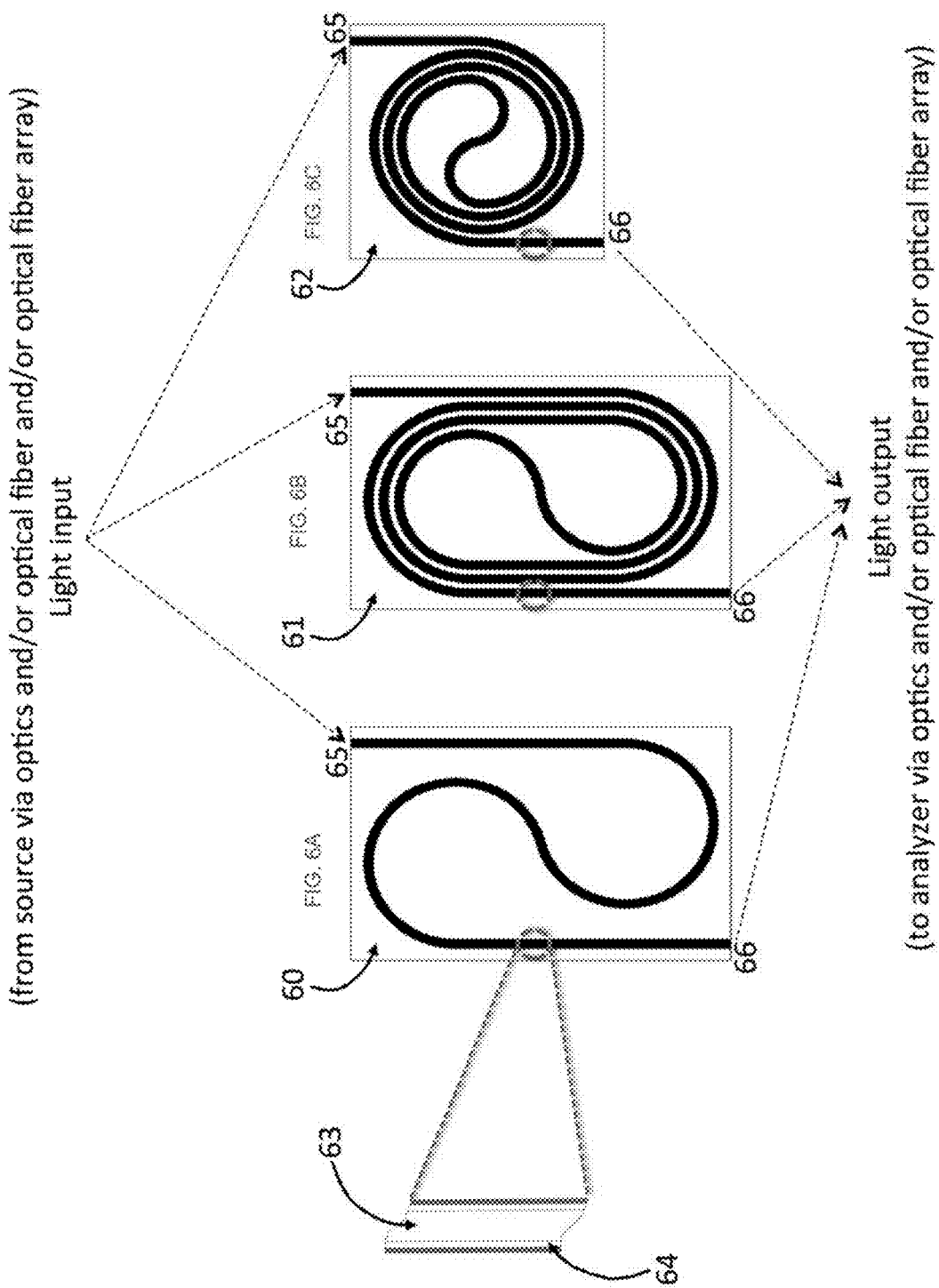
FIGS. 6A-6C are diagrammatic representations of several spiral type meandering hollow waveguide embodiments of the substrate-integrated hollow waveguide sensor.

Details of One Embodiment as a Meandering Hollow Waveguide for Use with Collimated and Non-Collimated Light in a Substrate-Integrated Hollow Waveguide Sensor FIGS. 6A-6C are diagrammatic representations of other configurations of meandering hollow waveguides 60, 61, 62 having, as one example, rectangular (2×2.1 mm) hollow channels 63 with a plurality of spiral type channel arrangements of varying lengths and/or numbers of spirals and having an internal channel surface treatment 64 and/or channel modifications chemo- or biolayers, immobilized enzymes, antigen/antibodies) such that the overall device can be coupled to a source and analyzer forming the basis of the substrate-integrated hollow waveguide sensor for conducting gas/vapor and/or liquid measurements performed remotely (e.g., via an optical fiber or fiber array or combinations that include optics) or non-remotely (e.g., optics) and/or in situ using, but not limited to, infrared absorption or Raman scattering spectroscopy techniques. The hollow channel of these meandering waveguide configurations serves as a miniature gas/vapor or liquid cell and as a 'light pipe' for directing and constraining the light and importantly for co-locating the light and analyte(s).

In operation, light from either a collimated (e.g., laser) or non-collimated (e.g. SiC, globar, etc.) source, is directed to one of two meandering waveguide channel ports 65 via a fiber or fiber array or conventional optics (not shown) or combinations thereof. Light entering the waveguide channel opening propagates through the hollow channels via interactions with the meandering waveguide channel surfaces. As the light traverses the entire path length of the hollow channels, it interacts with gas/vapor and/or liquid phase molecules co-located in the hollow channels via a plurality of ways to be discussed later (Section XII). Light exiting the waveguide channel port 66 is directed via a fiber or fiber array or conventional optics (not shown) or combinations thereof to the analyzer where interactions (e.g., absorption, Raman scattering) between the light and molecules are recorded. It is also important to note that either port of the FIG. 6A-6C meandering waveguide embodiments can serve as the light in-coupling or light out-coupling port from/to the source and analyzer, respectively.

The spiral type meandering waveguide design is an embodiment when the light in-coupled to the meandering waveguide channel port is not highly collimated i.e., diverging). The reason for this is in part due to the angles at which light is guided within the spiral type geometry. Ray trace modeling has shown that the spiral type geometry does not produce any back reflection of light. Additionally, some angles of light incidence within a meandering channel result in more throughput losses than others for specific optical coatings. As an example, for gold-coated meandering channel surfaces, the spiral type design minimizes grazing angle incidence relative to other types (e.g., serpentine type) of waveguide configurations.

Light divergence is a general characteristic of multimode optical fibers when used, for example, to guide light from the source to the meandering waveguide. Even when collimating optics are introduced, the light exiting the fiber is not highly collimated. It is possible to use collimating optics with single mode fibers for achieving highly collimated light, however, the small diameter of the single mode fiber greatly limits power throughput. Even so, the spiral type design is still usable with highly collimated in-coupled light although there are other embodiments (e.g., serpentine type) that may be advantageous in terms of power throughput and sensitivity for the same path length.

Light scattering, is another type of loss that occurs as the light interacts with the meandering channel surfaces. This can be minimized by polishing the channel surfaces down to a roughness that is much smaller than the wavelength(s) of light traversing the meandering waveguide (Note: here we are neglecting any scattering from the sample). For example, mid-IR light is on the order of one to several micrometers in wavelength. A channel roughness on the order of single microns would produce greater scattering losses compared to a channel roughness on the order of a few 100 nanometers. Fresnel losses are at a minimum when the f/numbers of the light coupled into the meandering waveguide and the meandering, waveguide itself are matched. Antireflective coatings can also be applied to optical elements to reduce Fresnel losses.

Figure 7:
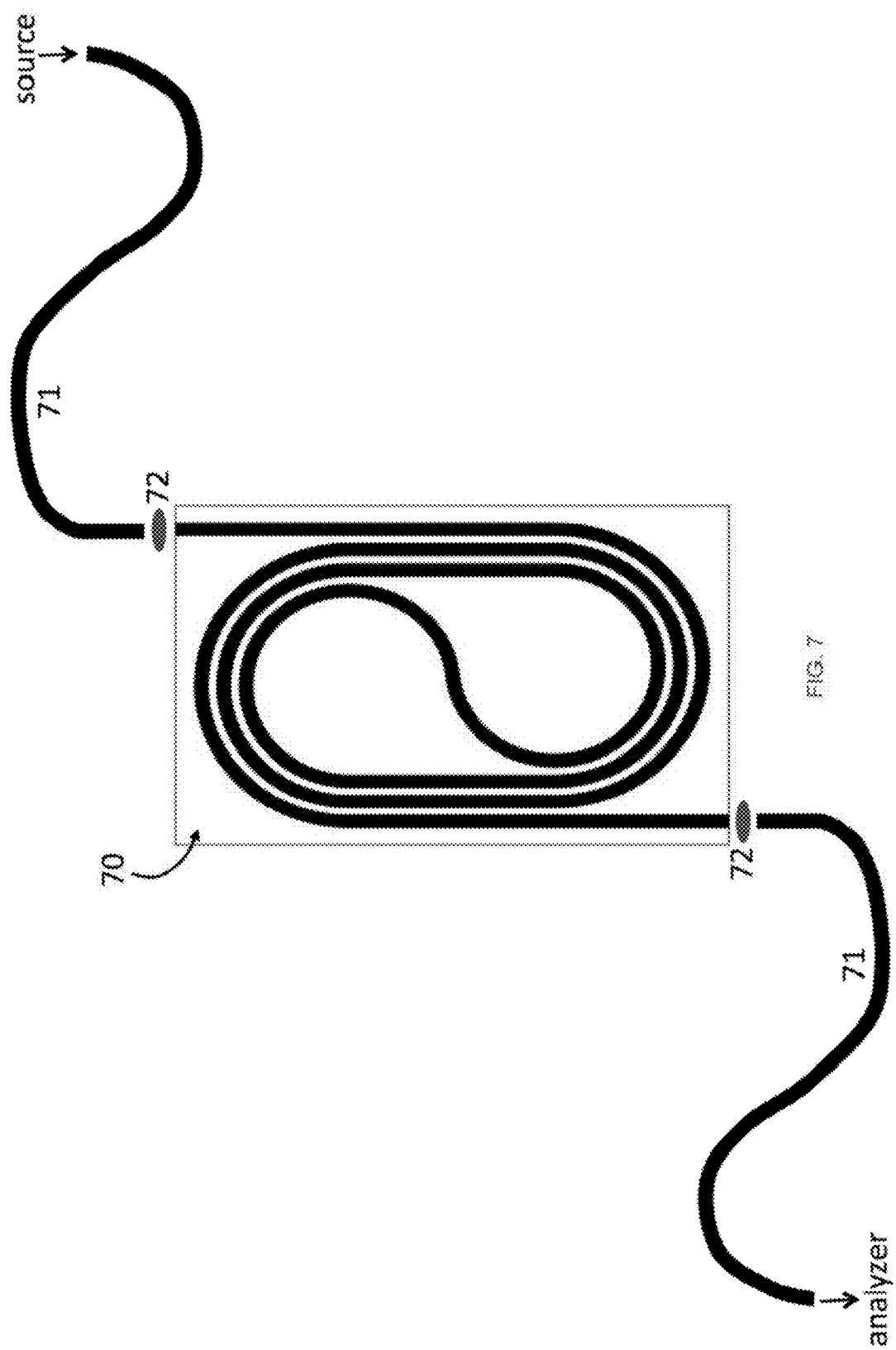
FIG. 7 is a diagrammatic representation of one of several embodiments of the substrate-integrated hollow waveguide sensor configured with the spiral type meandering hollow waveguide of FIG. 6B and having optical fiber couplings.

FIG. 7 is a diagrammatic representation of a spiral type meandering waveguide 70 (previously described in FIG. 6B and intended as a representation of the general spiral type meandering waveguide configuration) integrated to the source and analyzer using optical fibers and/or fiber arrays and/or a combination of fibers 71 and optics 72, forming the basis of the substrate-integrated hollow waveguide sensor. The type fibers and optical elements depicted in FIG. 7 are intended to be the same as previously described in an earlier section.

Figure 8:
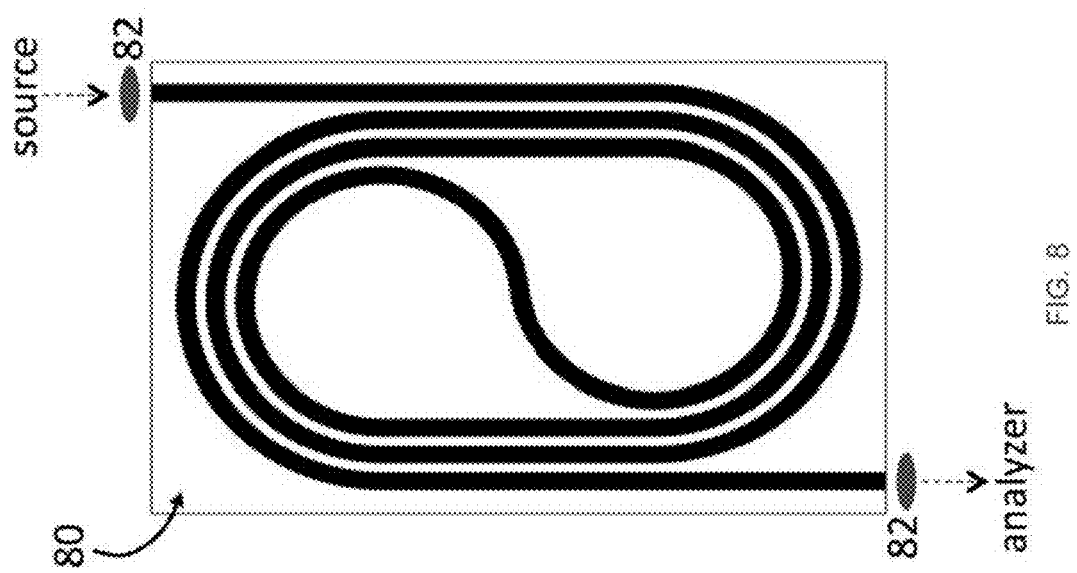
FIG. 8 is a diagrammatic representation of one of several embodiments of the substrate-integrated hollow waveguide sensor configured with the spiral type meandering hollow waveguide of FIG. 6B and having optical couplings.

FIG. 8 is a diagrammatic representation of the serpentine meander waveguide 80 (described in FIG. 6B) but without coupling fibers. Here optics 82 are used to interface the meander waveguide to the source and analyzer, forming the basis of the substrate-integrated hollow waveguide sensor. The type of optical elements depicted in FIG. 5 are intended to be the same as previously described in an earlier section.

Upon review of this disclosure, other embodiments will be apparent to those skilled in the art; the descriptions given are not intended to be restrictive. For example, an optic (e.g., reflector, grating, etc.) could be placed at one channel opening to direct light through the waveguide channel a second time forming a multi-pass (e.g double-pass in the simplest case) configuration.

Figure 4:
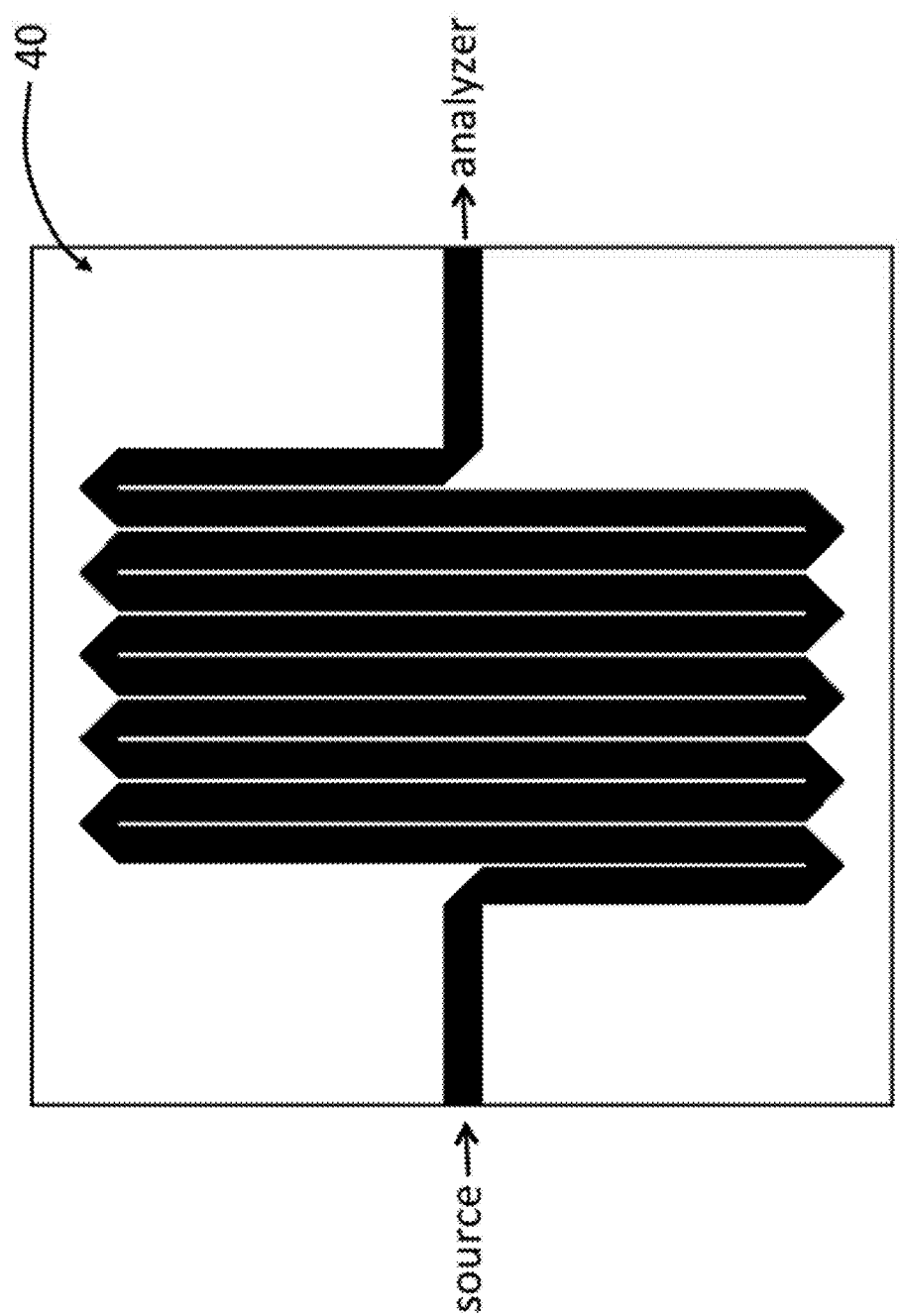
FIG. 4 is a diagrammatic representation of one of several alternate serpentine type meandering hollow waveguide embodiments of the substrate-integrated hollow waveguide sensor.

Details of One Embodiment as a Modular Meandering Hollow Waveguide for Use with Collimated or Non-Collimated Light in a Substrate-Integrated Hollow Waveguide Sensor A. Description and Assembly of the Modular Meandering Hollow Waveguide FIGS. 9A-1 through 9A-4 area diagrammatic representations (sub assemblies 1, 2, 3; unified waveguide) of a meandering hollow waveguide 90 having, as one example, more than one individual part 91, 92, 93 that upon assembly produces a unified waveguide 90 having, but not limited to, rectangular (2×2.1 min) hollow channels with, but not limited to, a spiral type channel configuration and having an internal surface treatment and/or channel modifications (e.g., chemo- or biolayers, immobilized enzymes, antigen/antibodies) such that the overall device can be coupled to a source and analyzer forming the basis of the substrate-integrated hollow waveguide sensor for conducting gas/vapor and or liquid measurements remotely (e.g., via an optical fiber or fiber way or combinations that include optics) or non-remotely (e.g. optics) and/or in situ using, but not limited to, infrared absorption or Raman scattering spectroscopy techniques. The hollow channel 94 formed by means of assembly of the individual parts, serves as a miniature gas/vapor or liquid cell and as a 'light pipe' for directing and constraining the light and importantly for co-locating the light and analyte(s).

The operation aspect of this type of device is similar to what has already been discussed for the spiral type meandering waveguides described in section IV; the operation aspect described in section III is also relevant here for other modular embodiments envisioned.

Independent of the meandering channel type (e.g., serpentine, straight, spiral, combinations, and variations of each) produced upon assembly of the more than one part, the dimensions of the more than one part could be predetermined along with the location of hollow channel ports to allow interchangeability. As an example, a similar spiral type meandering waveguide having a greater geometric path length (see the diagrammatic representation in FIG. 6B) could be assembled upon exchange of at least one individual part 92, 93. As another example, a serpentine type meandering waveguide (see the diagrammatic representation in FIG. 1) could be assembled upon exchange of at least one individual part 92, 93, (Note: 91 is a flat cover plate which does not have any effect on the channel geometry or path length.) Furthermore, the modularity/interchangeability is not limited to only meandering waveguide configurations wherein the light is in-coupled to one hollow meandering channel port and out-coupled via a different channel port (e.g., a single pass waveguide design). Other embodiments wherein the light is in-coupled and out-coupled via the same meandering channel port are also envisioned (e.g., multipass waveguide designs). Section VI describes a multipass hollow meandering waveguide design. The operation aspect of a multi-pass meandering waveguide will also be described in section VI.

Thus, having the capability to, interchange more than one part and thereby change the configuration of the meandering waveguide, essentially means that substrate-integrated waveguide sensors comprised of modular hollow waveguides are modular and interchangeable; a substrate-integrated waveguide sensor can be tailored to a specific sensing application by changing, at least one part of the meandering waveguide. This modularity could also extend to the source and analyzer making the substrate-integrated waveguide sensor tailorable in more than one application aspect.

The above examples describe how a sensor comprising a meandering waveguide could be quickly/rapidly adjusted/optimized to meet a plurality of sensitivity requirements by interchange of one or more individual parts. Rapid exchange is facilitated because optical realignment can be made inherent via predetermined dimensions and location of hollow channel opens of the more than one individual part.

There are numerous advantages of the modular more than one piece substrate-integrated hollow waveguide sensor comprising a plurality of meandering hollow waveguides over monolithic conventional hollow waveguide-based sensor prior art. These include: the ability to perform surface treatments and/or modifications on the open channels; inspection of the open channel; the ability to more easily add optical components (e.g., lenses, mirrors, gratings, retro-reflectors, optical fibers, angled optical components, windows, etc.); the ability to polish the channel surfaces using techniques not possible with monolithic hollow waveguides; the ability to utilize different coatings within the same waveguide device, the ability to incorporated other sensors (e.g., temperature, pressure, etc.) or non-optical components into the waveguide; the ability to incorporate valves and other peripheral components such that the waveguide can be fabricated as a flow cell; the ability to form 2-dimensional and 3-dimensional channel structures; and the ability to replace parts.

The detailed specifications of the invention described above and the reduction to practice shown should not be construed as limitations of the scope of the invention, but rather as one example of a embodiment. For those skilled in the art, other embodiments (e.g., serpentine, straight, spiral, combinations, and variations of each) will be apparent; the descriptions given are not intended to be restrictive.

B. Reduction to Practice: a Mid-Infrared, Gas/Vapor, Flow Cell, Sensor Comprised of a Modular Meandering Hollow Waveguide.

FIG. 9B is an image of a gas/vapor, flow cell, sensor comprising the spiral type, four-part, meandering hollow waveguide illustrated in FIGS. 9A-1 through 9A-4. For consistency, the numbering of individual parts 91, 92, 93 that comprise the unified waveguide 90 are maintained in FIG. 9B. In this reduction to practice, the image shows the meandering waveguide as a unified device 90 secured between the top 96 and bottom plates 97 of a custom clamping device (FIG. 9C-1 has been included to show the overlay of the meandering channel, with the clamping device). The hollow waveguide channel surfaces were gold coating to reflect mid-IR light. An optical window 95 (0.5 min thick, 0.25 inch diameter, BaF2) secured across both hollow channel ports 94 (only one is visible in the image) encloses the meandering waveguide producing an air-right seal. The enclosed channel serves as a miniature gas/vapor cell and as a 'light pipe' for directing and constraining the light and importantly for co-locating the light and analyte(s). Luer lock 98 valves partially visible in the image are used to control gas/vapor flow through the enclosed meandering channel via a pair of small access ports (not visible) fabricated into the top individual part 91 of the unified (meandering) waveguide.

Figure 9D:
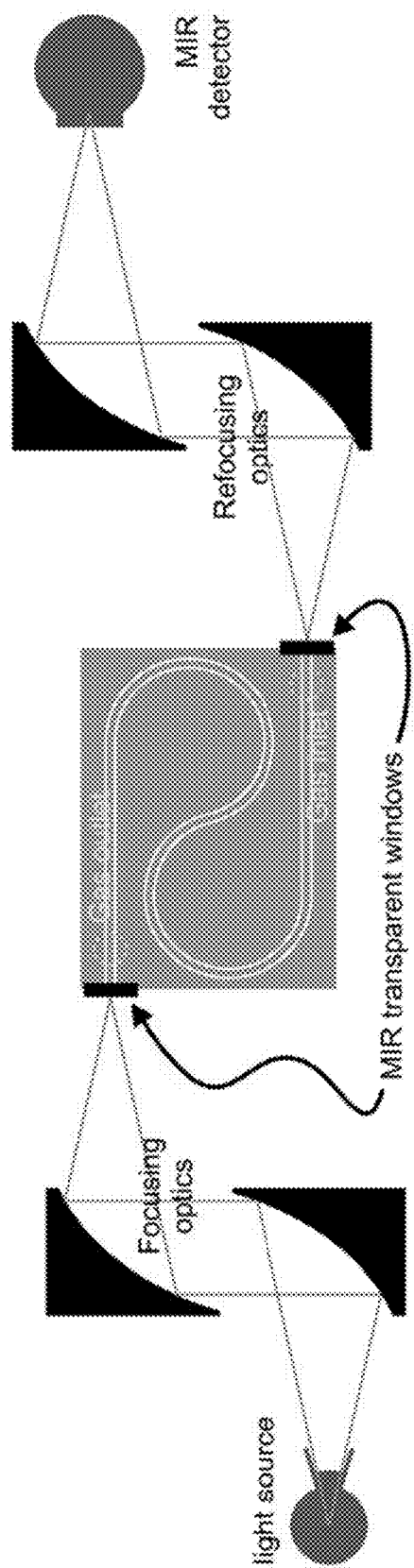
FIG. 9D is a diagrammatic representation of a prototype FTIR-based, flow cell, sensor for acquiring mid-IR spectra of gases/vapors.
Figure 9E:
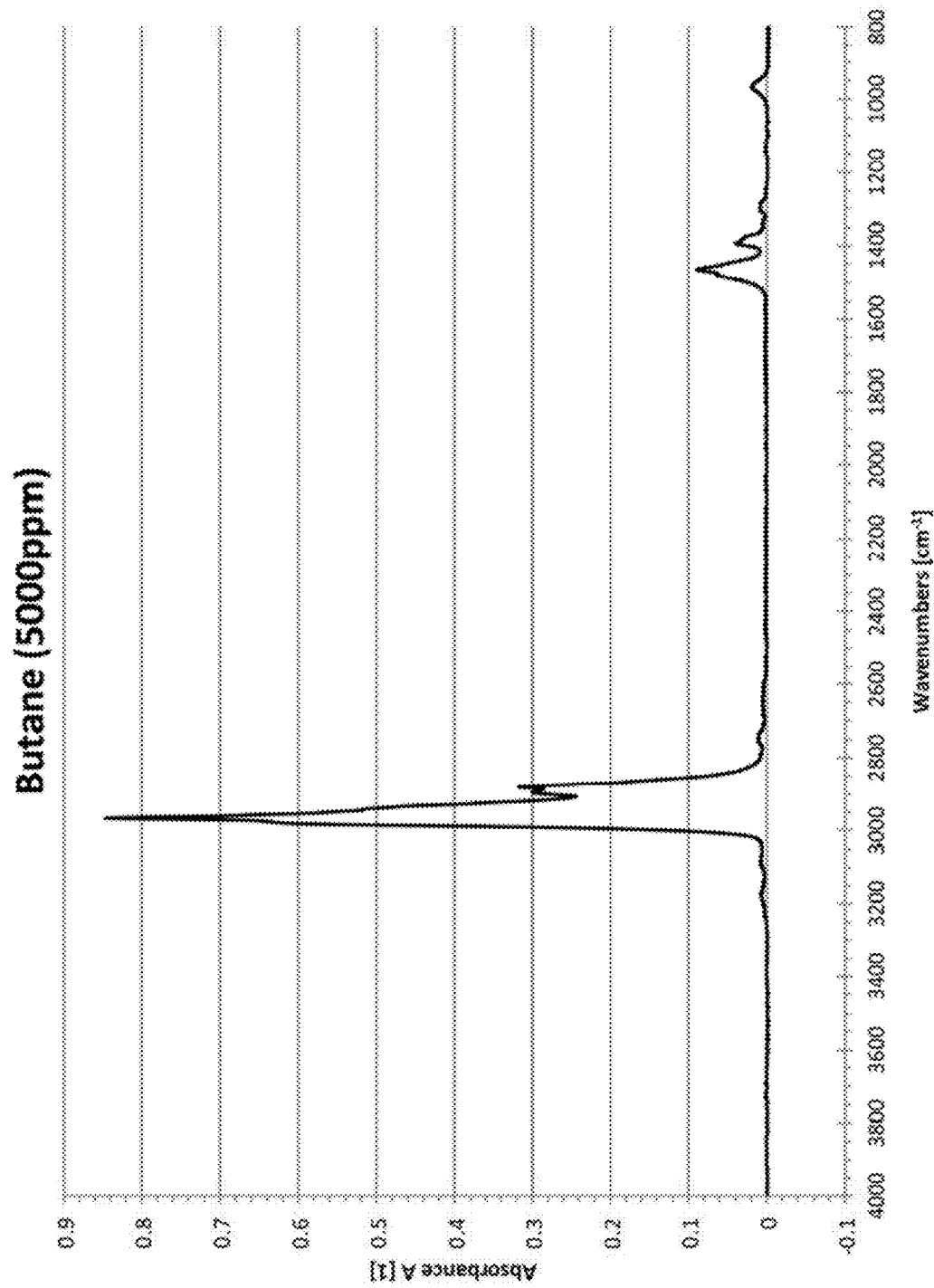
FIG. 9E is a mid-infrared FTIR spectrum of butane acquired with a sensor comprising a spiral type modular hollow waveguide.
Figure 9F:
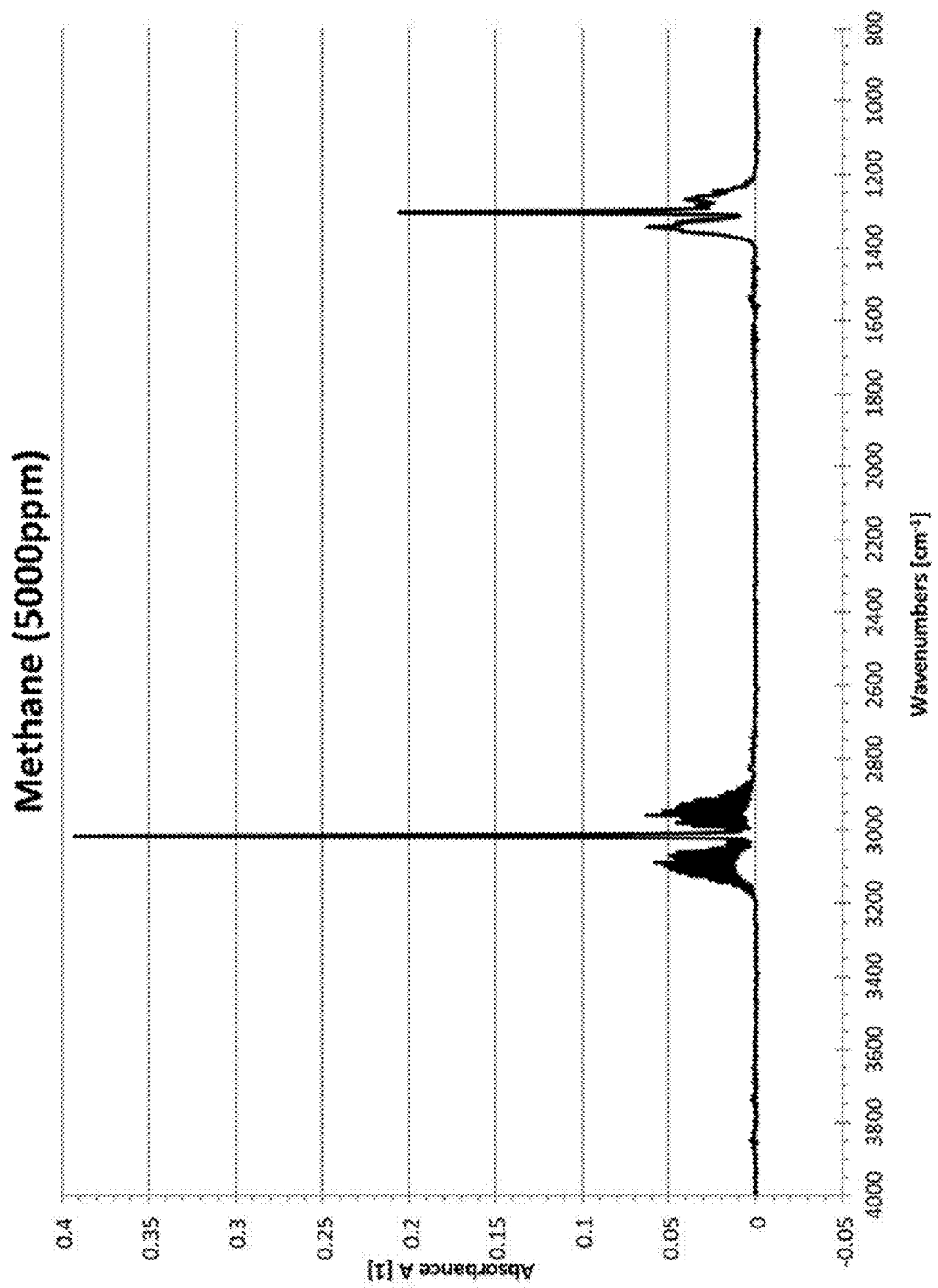
FIG. 9F is a mid-infrared FTIR spectrum of methane acquired with a sensor comprising a spiral type modular hollow waveguide.
Figure 9G:
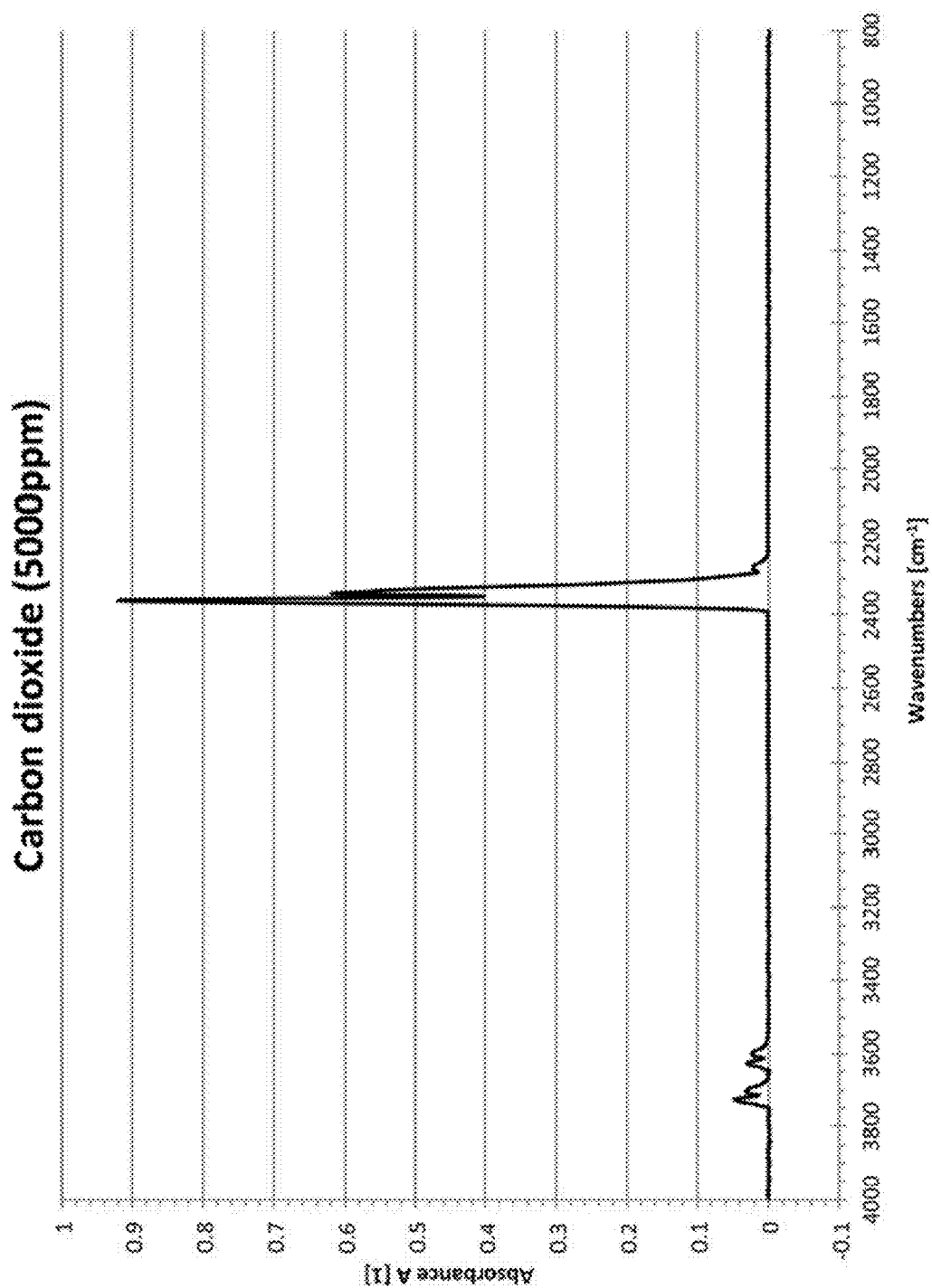
FIG. 9G is a mid-infrared FTIR spectrum of carbon dioxide acquired with a sensor comprising a spiral type modular hollow waveguide.

FIG. 9D is a diagrammatic representation of the experimental setup. Briefly, non-collimated light from an FTIR spectrometer source (i.e., SiC filament), was focused via a pair of off-axis parabolic mirrors to one of two hollow channel ports of the meandering waveguide. Light entering the meandering hollow waveguide first passed through an optical window before propagating via interactions with the meandering waveguide gold coated channel surfaces. Concurrently, a gas/vapor was flowed through the enclosed waveguide channel at a predetermined rate. Light that was not absorbed by the gas/vapor molecules (or attenuated otherwise via scattering or non-analyte absorption, etc.) then passed through a second optical window and was directed to an analyzer (e.g., an external MCT detector interfaced to the FTIR spectrometer). FIGS. 9e,f,g are mid-IR absorption spectra of butane, methane, and carbon dioxide gases, respectively, measured at a concentration of 5000 ppm, each with the mid-IR, flow cell, gas/vapor sensor.

The details of the reduction to practice described above should not be construed as limitations of the scope of the invention, but rather as one example of an embodiment and measurement technique. For example, light could also be coupled to the source and analyzer remotely (e.g., via an optical fiber or fiber array or combinations that include optics) or non-remotely (e.g., optics). For those skilled in the art, other embodiments and spectroscopic techniques (e.g., Raman scattering) be apparent; the descriptions given are not intended to be restrictive.

Details of One Embodiment as a Multi-Pass Meandering Waveguide for Collimated and Non-Collimated Light in a Substrate-Integrated Hollow Waveguide Sensor FIG. 10A is a diagrammatic representation of a multi-pass meandering hollow waveguide 100 having, as one example, rectangular (2×2.1 millimeter) hollow channels 110 with a plurality of spiral type channel arrangements of varying lengths and/or numbers of spirals and having an internal surface treatment 120 and/or channel modifications (e.g., chemo- or biolayers, immobilized enzymes, antigen/antibodies) such that the overall device can be coupled to a source and analyzer forming the basis of a substrate-integrated hollow waveguide sensor for conducting gas/vapor and/or liquid measurements performed remotely (e.g., fiber array, optics, or combinations) or non-remotely (e.g., optics) and/or in situ using, but not limited to, infrared absorption or Raman scattering spectroscopy techniques. Although the inner spiral channel of this meandering waveguide terminates, the hollow channel serves as a miniature gas/vapor or liquid cell and as a 'light pipe' for directing and constraining the light and importantly co-locating the light and analyte(s).

In operation, light from either a collimated (e.g., laser) or non-collimated (e.g., SiC, globar, etc.) source, is directed to one 130 of two meandering waveguide channel ports via a fiber or fiber array or conventional optics (not shown) or combinations thereof.

Light entering the meandering hollow waveguide propagates via interactions with the meandering waveguide channel surface toward the innermost spiral of the meandering waveguide until reaching a termination point 140. The propagation direction of the light is reversed at the termination point 140 via any one of a number of optical elements (e.g., retro-reflector, mirror, grating, etc.) and the light passes more than once through the waveguide channel. As the light traverses the entire path length of the hollow channel in either direction, it interacts with gas/vapor and/or liquid phase molecules co-located, in the hollow channels via a plurality of ways to be discussed later (Section XII). Light exiting the waveguide channel port 130 is directed via a fiber or fiber array or optical elements not shown) or combinations thereof to the analyzer where interactions (e.g., absorption, Raman scattering) between the light and molecules are recorded.

This meandering waveguide configuration can also be described as a multi-pass or, in this embodiment, double-pass waveguide design since light traverses the meandering waveguide channel more than once. An advantage of the multi-pass meandering design is increased optical path length within the same meandering waveguide channel volume and dimensions (e.g., in this case, 5×5 centimeters) as a similar device designed to allow light to traverse once. As an example, appendix. A details the geometrical channel length calculation for the FIG. 10 meandering waveguide. This calculation assumes a central ray passing down the center of the meandering waveguide channel and only interacting at the inner spiral termination point 140 with an optical element 140 (i.e., never interacting with the channel surfaces). The calculated spiral channel geometric length of 299.89 millimeters is, of course, less than the true optical path length of a light ray traveling from the meander waveguide port 130 to the termination point 140 of the inner spiral because this calculation estimate does not, take into account the added path length provided by reflections along the treated channel surface in both direction. Nonetheless, this is a useful (conservative) estimate for demonstrating that a total optical path length estimate of 599.79 millimeters (2×299.89 millimeters) is achievable within a 50×50 millimeter form factor. Note: this is one of several spiral type waveguide configurations reduced to practice; FIGS. 10B and 10C show images of an uncoated spiral type waveguide made from aluminum alloy and a polished gold-coated plate, respectively. When combined, the FIGS. 10B and 10C elements form an enclosed meandering waveguide. A substrate integrated hollow waveguide sensor comprising this hollow waveguide configuration would require a form factor of 50 millimeters centimeters for the waveguide component. For comparison, a similar sensor comprising a conventional (straight) hollow waveguide of equivalent optical path length, and for a central ray propagating down the center, would require the full 599.79 millimeters in length.

FIG. 11 is a diagrammatic representation of an alternate spiral type meandering hollow waveguide 200 (similar to that described in FIG. 10) wherein the termination point 210 of the innermost spiral channel is open (i.e., a port) such that light can be coupled into or out of the meandering hollow waveguide. This can be accomplished via an optical element (e.g., mirror, reflector, grating, etc.) that directs the light out of plane from the waveguide propagation length. This meandering waveguide configuration utilizes different planes of light propagation. Such an embodiment makes possible meandering waveguide scaffolding (e.g., stacking) or utilization of more than one waveguide as part of a substrate-integrated hollow waveguide sensor.

Details of One Embodiment as a Straight Type Meandering Hollow Waveguide for Use with Collimated or Non-Collimated Light in a Substrate-Integrated Hollow Waveguide Sensor.

FIG. 12 is a diagrammatic representation of a meandering hollow waveguide 300 having, as examples, square hollow channels 310 with a plurality of channel dimensions and having an internal channel surface treatment and/or channel modifications (e.g., chemo- or biolayers, immobilized enzymes, antigen/antibodies) such that the overall device can be coupled to a source and analyzer forming the basis of the substrate-integrated hollow waveguide sensor for conducting gas/vapor and/or liquid optical measurements, performed remotely (e.g., coupling via an optical fiber or fiber May or combinations that include optics) or non-remotely (e.g., coupling via optics) and for in situ using, but not limited to, infrared absorption or Raman scattering spectroscopy techniques. The hollow channel of the meandering waveguide serves as both a miniature gas/vapor or liquid cell and as a 'light pipe' for directing and constraining the light and importantly for co-locating the light and analyte(s). The operation aspect of this type device is similar to what has already been discussed for the serpentine type meandering waveguides described in section III. An optic (e.g., reflector, grating etc.) could be placed at one channel opening to direct light through the waveguide channel a second time forming a multi-pass (e.g double-pass in the simplest case) configuration.

Details of One Embodiment as a Substrate-Integrated Meandering Waveguide Sensor Comprising the Source, Meandering Waveguide, Analyzer as a Monolith Device.

Figure 13:
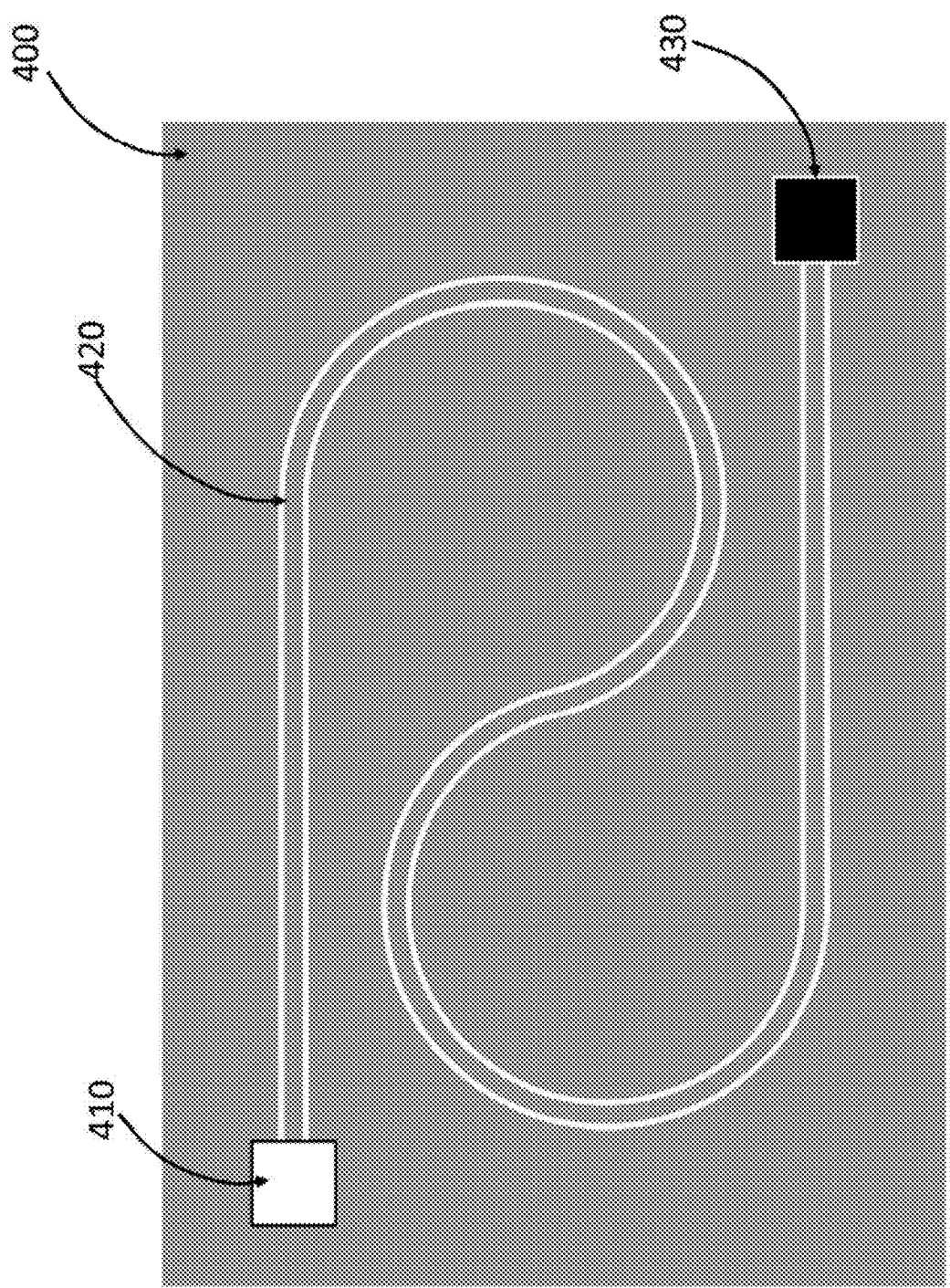
FIG. 13 is a diagrammatic representation of a monolithic substrate-integrated hollow waveguide sensor embodiment.

FIG. 13 is a diagrammatic representation of a substrate-integrated hollow waveguide sensor 400 wherein the light source 410, meandering waveguide channel 420, detector 430 are fabricated by way of monolithic silicon micromachining and housed in an enclosure with light guiding optics (not shown). The operation aspect of this meandering waveguide is similar to what has already been discussed for the spiral type meandering waveguides described in section IV.

Figure 14:
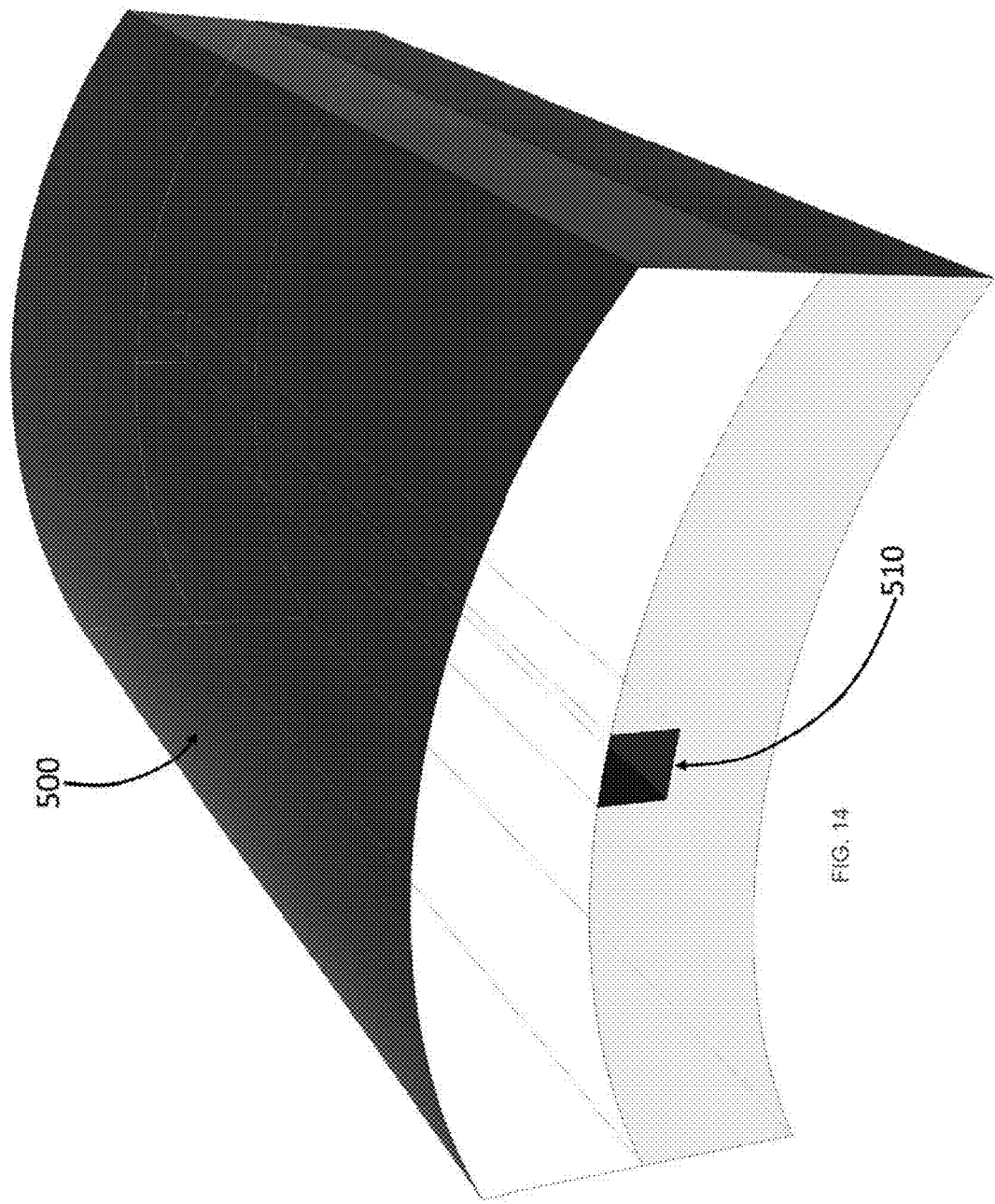
FIG. 14 is a diagrammatic representation of a generic non-planar meandering hollow waveguide.

Details of One Embodiment as a Non-Planar Hollow Meandering, Waveguide for Collimated or Non-Collimated Light in a Substrate-Integrated Meandering Waveguide Sensor FIG. 14 is a diagrammatic representation of a generic (i.e., any of, but not limited to straight; serpentine; spiral-type; combinations of) non-planar meandering hollow waveguide 500 having, as an example, a rectangular (2×2.1 millimeter) hollow channel 510 and having an internal channel surface treatment and/or channel modifications (e.g., chemo- or biolayers, immobilized enzymes, antigen/antibodies) such that the overall device can be coupled to a source and analyzer forming the basis of the non-planar substrate-integrated hollow waveguide sensor for conducting gas/vapor and/or liquid optical measurements, performed remotely (e.g., coupling via an optical fiber or fiber array or combinations that include optics) or non-remotely (e.g., coupling via optics) and/or in situ using, but not limited to, infrared absorption or Raman scattering spectroscopy techniques. The hollow channel of the meandering waveguide serves as both a miniature gas/vapor or liquid cell and as a light pipe for directing and constraining the light and importantly for co-locating the light and analyte(s). The operation aspect of this generic waveguide is dependent on the specific hollow channel configuration and is similar to what has already been discussed in sections III, IV, VI. An optic (e.g., reflector, grating, etc.) could be placed at one channel opening to direct light through the waveguide channel a second time forming a multi-pass configuration.

Details of Materials for Making Substrate-Integrated Hollow Waveguide Sensors Comprising Meandering Hollow Waveguides The following applies for any of the meandering waveguide embodiments presented. The meandering waveguides are made from any of but not limited to the following: polymers (e.g., PEEK, PC, PMMA, PTFE, FEP); metals (e.g. aluminum, stainless steel, brass, copper, gold, silver, nickel); semiconductor materials (e.g., silicon, III-V compound semiconductors, II-VI compound semiconductors, germanium, silicon germanium); dielectrics (e.g., $SiO_x$, $Si_xN_y$); and biodegradable materials (e.g., polylactate).

Details of Meandering Waveguide Channel Dimensions and Geometries

Figure 16:
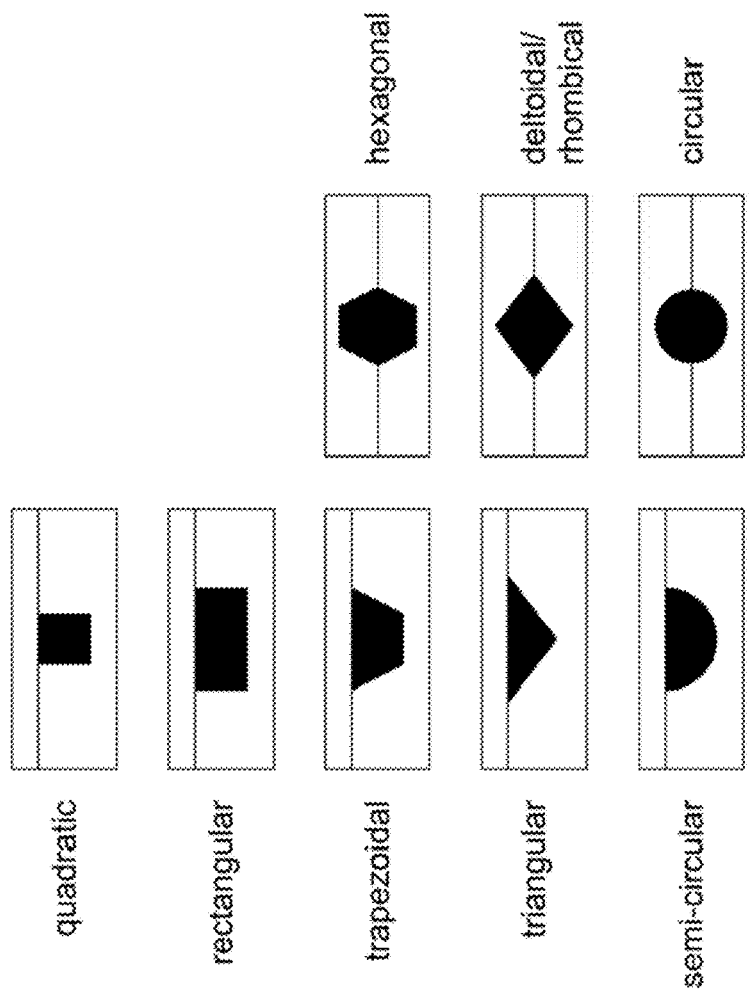
FIG. 16 is a diagrammatic representation of one of several meandering hollow waveguide channel geometries.

The hollow channel of the meandering waveguide may be of different path lengths and the channel cross sections may be greater or less than the 2×2.1 millimeter or other dimensions disclosed herein. Tapered hollow channels of many types are also envisioned as illustrated in FIG. 15A-L for, as an example, matching the channel size to a detector element. Furthermore, the channel cross-sectional geometries can be any of, but not limited to the illustrations of FIG. 16. Thus, substrate-integrated hollow waveguide sensors comprising meandering hollow waveguides ma also be of different path lengths, channel cross sections, and channel geometric configurations and have tapered or widened/expanded channels (refer to FIG. 15A-L) and/or combinations thereof.

Details of Techniques for Fabricating Substrate-Integrated Hollow Waveguide Sensors Comprising Meandering Hollow Waveguides The techniques and/or combinations thereof for fabricating meandering waveguides are any of but are not limited to mechanical machining (e.g., drilling, milling, grinding, press-molding, embossing, die-casting, laser cutting/welding, electric discharge machining (EDM) and microfabrication e.g., reactive ion etching (REE) inductively coupled plasma-reactive ion etching (ICP-RIE), wet etching, and focused ion beam (FIB)). Some of the aforementioned fabrication techniques and/or combinations thereof produce the waveguide channels but necessitate waveguide surface treatment for removing undesirable surface features such as tooling marks that lead to decreased waveguide performance. The waveguide surface treatment may involve any of but not limited to cleaning, polishing and applying coatings. Waveguide polishing techniques may include, but are not limited to, the following: mechanical, chemo-mechanical, chemical, and electrochemical. Waveguide coating techniques include any of but not limited to the following: wet chemistry, electrochemistry, galvanics, physical deposition (e-beam evaporator, sputterer, thermal evaporator, MBE, etc.), chemical deposition (PECVD, CVD, MOCVD, etc.), and plasma deposition. The waveguide coatings are made from, any of, but not limited to the following: metal coatings (e.g., Au, Al, Ag, dielectrics, Pt, Cr, Ni, Cu; dielectric, optical transparent coatings (e.g., AgI, AgBr, ZnSe and combinations); polymer coatings (e.g., teflon, ethylene/propylene co-polymer, polybutadiene). Other types of waveguide surface modifications include, but are not limited to the application of chemo- and biolayers, immobilized enzymes, and antigen/antibodies. The fabrication and final preparation of waveguides may involve any combination of the aforementioned techniques and steps.

Details of Mechanical and Thermal Support and Stabilization of Substrate-Integrated Hollow Waveguide Sensors Comprising Meandering Hollow Waveguides Referring again to FIG. 9B of the drawings is an image of as custom clamping device 96, 97 for support, stabilization, and alignment maintenance of the modular meandering waveguide during operation. The key physical requirements of the clamp are as follows: (1) sufficient clamping force to eliminate gaps between the individual parts for maximizing power throughput; (2) sufficient clearance to allow ease of access to the meandering hollow waveguide channel ports for light in- and out-coupling via fibers or arrays of fibers or conventional optics; (3) expandability along the z-axis to allow any of but not limited to: heating sources, insulating materials, additional (stacked) meandering hollow waveguides; (4) kinematic features to allow quick assembly and/or alignment of any of but not limited to: heating source, thermal insulating materials, additional (stacked) meandering hollow waveguides; (5) lightweight construction materials to minimize size/weight; 6) mechanically stable to maintain mode structure of propagating light within the meandering hollow waveguide; and (7) an ergonomic design that allows ease of interchanging and/or replacing components. For certain sensing applications (e.g., harsh environments, high pressure, high temperature, etc.) additional requirements may include: (1) chemical resistance; (2) thermal resistance; (3) thermal stability; and (4) thermal dissipation properties.

Figure 17:
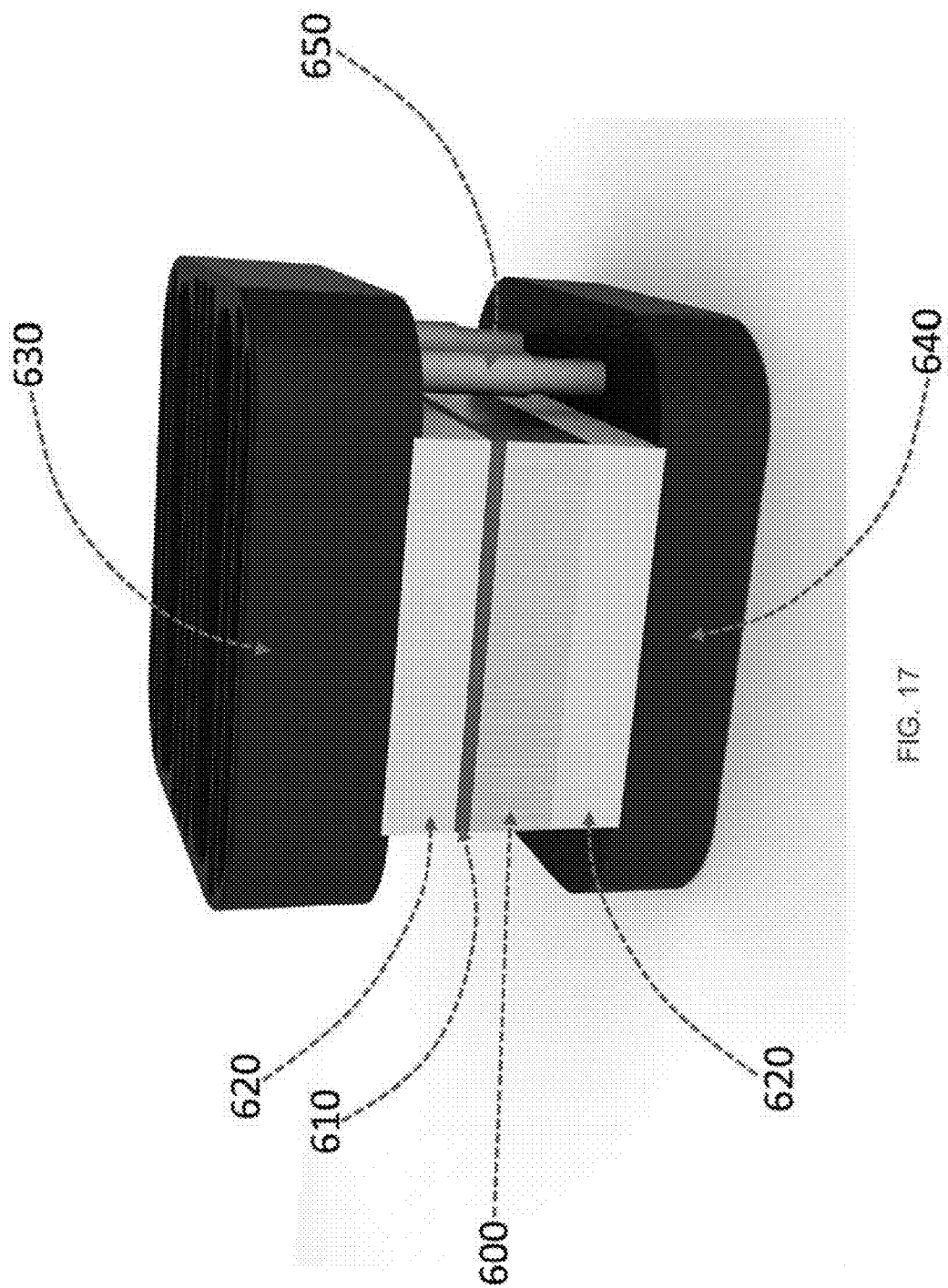
FIG. 17 is a diagrammatic, representation of a clamping device supporting a meandering hollow waveguide with thermal control.

TABLE 1 lists the mechanical design parameters of a possible meandering hollow waveguide-clamping device. Both polycarbonate and aluminum alloy clamps were fabricated and tested with the latter yielding the better results mainly because of superior mechanical and thermal properties (see TABLE 2) including the ability to better minimize gaps between the meandering hollow waveguide comprised of four parts. FIG. 17 is a diagrammatic representation of a meandering hollow waveguide 600 (e.g., serpentine, spiral, folded, tapered, straight, and combinations and variations thereof), heating layer 610 (e.g., heating foil), thermal insulation layers 620 (e.g., foams, ceramics; in this case: ceramic fiber), secured between the top 630 and bottom aluminum alloy plates 640 of an anodized aluminum clamp having 6 mm screws 650. Mechanical stress simulations (not shown) and temperature distribution simulations (See TABLE 3 summary) were performed to determine an approximate design definition for meeting the clamp requirements. The results indicate that it is feasible to achieve homogenous internal meandering hollow waveguide temperatures in the range of 127.2° C. and 127.7° C. and maintain external clamp temperatures below 40° C. with 10 W of constant power supplied to the meandering hollow waveguide 600 via a heating foil 610. This embodiment provides thermal control of the meandering hollow waveguide device for any of but not limited to: thermal stability of the sensor under various and changing environmental conditions; thermal desorption of chemi- and/or physisorbed analytes within the hollow channels; and temperature control to mitigate the risk of condensates forming on surfaces within the hollow channels of the meandering waveguide. The addition of thermocouples or other miniature temperature sensors and/or pressure transducers (not shown) is also envisioned.

TABLE 1

Mechanical design parameters of a clamping device

| | |
|---|---|
| size capacity | 5.0 × 7.5 cm |
| design clamping force (axial load; compression force) | 19.62 kN |
| clamp material | Aluminum alloy (EN AW 7065 T65I) |
| screw size | M6 (grade 8.8) |
| number of screws | 4 |
| realized factor of safety (clamping force) | 1.93 |
| design (operating) temperature | 130° C. |

TABLE 2

Aluminum alloy clamp (EN AW 7075)

Alloy composition (main)

| | |
|---|---|
| Zn | 5.1-6.1 weight % |
| Mg | 2.1-2.9 weight % |
| Cu | 1.2-2.0 weight % | http://asm.matweb.com/search/
SpecificMaterial.asp?bassnum=MA7075T6
http://www.smh-metalle.de/internet/media/smh/pdf/
datenblatt/datenblatt_en_aw_7075_w.pdf
http://www.abmkupral.hu/
download/AW_7075_-_AlZn5,5MgCu.pdf Physical properties

| | |
|---|---|
| Density | 2.81 g/cm$^3$ | http://asm.matweb.com/search/
SpecificMaterial.asp?bassnum=MA7075T6
* the other 2 references have slightly different values
(namely 2.80 g/cm$^3$)

Mechanical properties

| | |
|---|---|
| Ultimate tensile strength | 572 MPa |
| Tensile yield strength | 503 MPa |
| Young's modulus (modulus of elasticity) | 71.7 GPa |
| Poisson's ratio | 0.33 | http://asm.matweb.com/search/
SpecificMaterial.asp?bassnum=MA7075T6
* the other 2 references have slightly different values Thermal properties

| | |
|---|---|
| Thermal expansion coefficient (@ 20° C.) | 23.6 μm/(m K) |
| Specific heat capacity | 0.96 J/(g K) |
| Thermal conductivity | 130 W/(m K) |
| Melting point (solid-liquid) | 477-635° C. | http://asm.matweb.com/search/
SpecificMaterial.asp?bassnum=MA7075T6
* the other 2 references have slightly different values

TABLE 3

Temperature/heat transfer modeling parameters

| | |
|---|---|
| Power transfer to iHWG | 10 W |
| ambient temperature | 20° C. |
| clamp temperature (target) | ≤40° C. |
| iHWG final temperature (target) | 120° C. | iHWG = acronym for integrated meandering hollow waveguide
NOTE:
The heat transfer simulation did not include applied pressure (i.e. clamping, force).

Although the meandering hollow waveguide with clamping device is one embodiment, this arrangement is not desirable for many sensing applications, particularly those constrained by weight and size limitations. Referring again to FIG. 10A of the drawings is a diagrammatic representation of a multi-pass meandering hollow waveguide 100 having shallow grooves 130. These channels enable the use of adhesives, which can be applied to the perimeter and central portions of the meandering waveguide 100 for permanently bonding the more than one parts resulting in a unified waveguide. Additionally, other techniques are envisioned for support, stabilization and alignment maintenance including any of but not limited to: screwing/bolting together, welding, brazing, pressing, and annealing.

Figure 18:
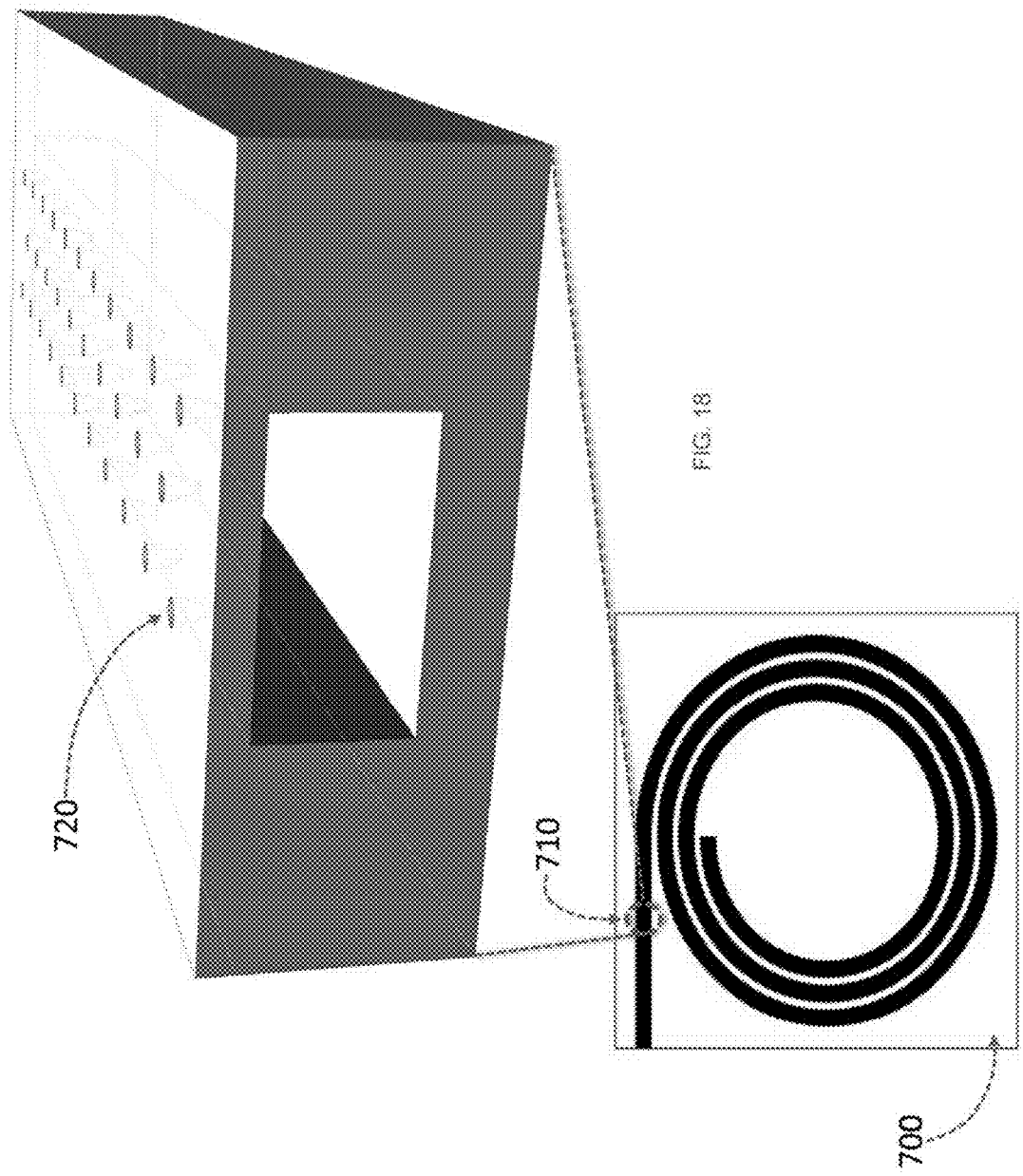
FIG. 18 is a diagrammatic representation of a meandering hollow waveguide having pores for vas exchange.

Details of Co-Locating the Analyte with Light in the Meandering Waveguide Channel Aside from those already disclosed herein, there are additional ways in which molecules (e.g., gas/vapor, liquid) are co-located with light inside the meandering waveguide hollow channels including, but not limited to diffusion controlled gas exchange via permeable nano- and/or micropores located at a plurality of positions within the meandering waveguide and passive diffusion via gaps between the guiding optics located at meandering channel ports. FIG. 18 is a diagrammatic representation of a multi-pass meandering hollow waveguide 700 wherein the straight channel section 710 of the spiral design includes nano- or micro-pores 720 far allowing gas exchange (e.g., effusion, diffusion) between environment and the inside of the hollow channel. Upon review of this disclosure, other embodiments will be apparent to those skilled in the art; the descriptions given are not intended to be restrictive. For example nano- or micro-pores could be located along any meandering section length and along some or all channel surfaces side walls, top or bottom walls).

The foregoing description of the invention has been presented for purposes of illustration and description and is not intended to be exhaustive or to limit the invention to the precise form disclosed. Many modifications and variations are possible in light of the above teaching. The embodiments disclosed were meant only to explain the principles of the invention and its practical application to thereby enable others skilled in the art to best use the invention in various embodiments and with various modifications suited to the particular use contemplated. The scope of the invention is to be defined by the following claims.

We claim:

1. A substrate integrated hollow waveguide, comprising:
at least one substrate layer;
a hollow channel formed in one or more layers of said at least one substrate layer, wherein said hollow channel is curved, wherein said channel comprises a light input port and a light output port, wherein said hollow channel extends from said light input port to said light output port, wherein a surface of said hollow channel is reflective to one or more predetermined wavelengths of light, wherein said at least one substrate layer comprises a first layer, a second layer in direct contact with said first layer and a third layer in direct contact with said second layer, wherein said first layer and said second layer and said third layer are attached together only with one or more removeable fasteners such that said first layer and said second layer and said third layer can be assembled together and disassembled, wherein said second layer is interchangeable with at least one alternate configuration of said second layer, wherein said second layer comprises a plurality of integral, non-contacting sections that fit together to define the opening of said channel in said second layer, wherein said opening extends in a first dimension from said first layer to said third layer and in a second dimension from said light input port to said light output port, and wherein said hollow channel along the entire length of said hollow channel supports only multimode propagation for said one or more predetermined wavelengths of light.

2. The waveguide of claim 1, further comprising a light source configured to provide said one or more predetermined wavelengths of light.

3. The waveguide of claim 2, further comprising means for directing said one or more predetermined wavelengths of light into said light input port, wherein said one or more predetermined wavelengths of light propagates within said channel and out of said light output port.

4. The waveguide of claim 3, further comprising an optical analyzer configured to analyze said one or more predetermined wavelengths of light that exits said light output port, wherein said optical analyzer is selected from the group consisting of a wavelength selection device and a frequency selection device.

5. The waveguide of claim 2, further comprising means for scanning the wavelength of said one or more predetermined wavelengths of light from said light source.

6. The waveguide of claim 1, wherein said at least one substrate layer is rigid.

7. The waveguide of claim 1, further comprising a light source and an optical analyzer integrated into said at least one substrate layer.

8. The waveguide of claim 1, wherein at least one substrate layer of said third at least one substrate layer comprises pores for gas to enter said channel.

9. The waveguide of claim 1, wherein said channel comprises a cross section having a geometric shape selected from the group consisting of quadratic, rectangular, trapezoidal, triangular, semi-circular, pentagonal, hexagonal, deltoidal/rhombical, circular, elliptical, oval, simple polygonal.

10. The waveguide of claim 1, wherein said channel comprises at least one of (i) added materials selected from the group consisting of a gas, a vapor and a liquid or (ii) a surface treatment selected from the group consisting of a reflective layer, a chemo-layer, a biolayer, an immobilized enzyme, an antigen and an antibody.

11. The waveguide of claim 1, further comprising means for allowing a gas to enter said hollow channel.

12. The waveguide of claim 1, wherein said channel is inwardly spiraling from said light input channel to a reflector, wherein said light input port and said light output port are co-located.

13. The waveguide of claim 1, further comprising a reflector of said one or more predetermined wavelengths of light operatively and fixedly placed such that said light entering said light input port will propagate in said hollow channel until said light reaches said reflector and will be reflected by said reflector to propagate in said hollow channel back to said light output port, wherein said light will exit said light output port, wherein said reflector is a plane reflector or a retro-reflector.

14. The waveguide of claim 1, wherein said first dimension is orthogonal to said a second dimension, wherein said both transverse dimensions of said hollow channel along the entire length of said hollow channel are orthogonal.

15. A method for fabricating a substrate integrated hollow waveguide, comprising:
providing at least one substrate layer;
forming a hollow channel in one or more layers of said at least one substrate layer, wherein said hollow channel is curved, wherein said channel comprises a light input port and a light output port, wherein said hollow channel extends from said light input port to said light output port, wherein a surface of said channel is reflective to one or more predetermined wavelengths of light, wherein said at least one substrate layer comprises a first layer, a second layer in direct contact with said first layer and a third layer in direct contact with said second layer, wherein said first layer and said second layer and said third layer are attached together only with one or more removeable fasteners such that said first layer and said second layer and said third layer can be assembled together and disassembled, wherein said second layer is interchangeable with at least one alternate second layer configuration, wherein said second layer comprises a plurality of integral, non-contacting sections that fit together to define the opening of said channel in said second layer, wherein said opening extends in a first dimension from said first layer to said third layer and in a second dimension from said light input port to said light output port, and wherein said hollow channel along the entire length of said hollow channel supports only multimode propagation for said one or more predetermined wavelengths of light.

16. The method of claim 15, further comprising providing a light source configured to provide said one or more predetermined wavelengths of light.

17. The method of claim 16, further comprising providing means for directing said one or more predetermined wavelengths of light into said light input port and further comprising means for directing said predetermined wavelengths of light out of said light output port.

18. The method of claim 17, further comprising providing an optical analyzer configured to analyze said one or more predetermined wavelengths of light that exits said light output port, wherein said optical analyzer is selected from the group consisting of a wavelength selection device and a frequency selection device.

19. The method of claim 15, wherein said at least one substrate layer is rigid.

20. The method of claim 15, further comprising integrating a light source and an optical analyzer into said at least one substrate layer.

21. The method of claim 15, further comprising forming pores in said third at least one substrate layer for gas to enter said hollow channel.

22. The method of claim 15, further comprising treating the said surface of said channel with a surface treatment selected from the group consisting of a reflective layer, a chemo-layer, a biolayer, an immobilized enzyme, an antigen and an antibody.

23. The method of claim 16, further comprising scanning the wavelength of said light from said light source.

* * * * *